(12) United States Patent
Xing et al.

(10) Patent No.: US 6,376,747 B1
(45) Date of Patent: Apr. 23, 2002

(54) PLANT-DERIVED MAP KINASE KINASE

(75) Inventors: Ti Xing; Kamal Malik, both of Ottawa; Teresa Martin-Heller, Gloucester; Brian L. Miki, Ottawa, all of (CA)

(73) Assignee: Her Majesty the Queen in right of Canada as represented by the Minister of Agriculture and Agri-Food Canada (CA)

( * ) Notice: Subject to any disclaimer, the term of this patent is extended or adjusted under 35 U.S.C. 154(b) by 0 days.

(21) Appl. No.: 09/384,162

(22) Filed: Aug. 27, 1999

(51) Int. Cl.$^7$ .................. C12N 15/09; C12N 15/29; C12N 15/82; A01H 5/00
(52) U.S. Cl. .................. 800/279; 800/278; 800/289; 800/298; 800/317; 800/317.4; 536/23.1; 536/23.2; 536/23.6; 435/69.1; 435/320.1; 435/468; 435/419
(58) Field of Search ................... 800/279, 278, 800/289, 298, 317, 317.4; 536/23.1, 23.2, 23.6; 435/69.1, 320.1, 469, 419

(56) References Cited

U.S. PATENT DOCUMENTS

| | | | |
|---|---|---|---|
| 5,494,813 A | * 2/1996 | Hepher et al. | 435/172.3 |
| 5,663,314 A | 9/1997 | Seger et al. | 536/23.2 |
| 5,837,815 A | 11/1998 | Lev et al. | 530/350 |
| 5,837,819 A | 11/1998 | Matsuomoto et al. | 530/350 |
| 5,986,082 A | * 11/1999 | Uknes et al. | 536/23.6 |

OTHER PUBLICATIONS

Hardin, S.C. et al., Molecular cloning and characterization of maize ZmMEK1, a protein kinase with a catalytic domain homologous to mitogen– and stress–activated protein kinase kinases, *Planta* 206, pp. 577–584 (1988).

Ichimura, K. et al., Molecular Cloning and Characterization of Three cDNAs Encoding Putative Mitogen–activated Protein Kinase Kinases (MAPKKs) in *Arabidopsis thaliana*, *DNA Research* vol. 5, No. 6, pp. 341–348 (1998).

Kovtun, Y. et al., Supression of auxin signal transduction by a MAPK cascade in higher plants, *Nature*, vol. 395, pp. 716–720 (10/98).

Nishihama, R. et al., Plant Homologues of Components of MAPK (Mitogen–Activated Protein Kinase) Signal Pathways in Yeast and Animal Cells, *Plant Cell Physiol.*, 36(5), pp. 749–757 (1995).

Shibata, W. et al., A tobacco protein kinase, NPK2, has a domain homologous to a domain found in activators of mitogen–activated protein kinases (MAPKKs), *Molecular and General Genetics*, 246, pp. 401–410 (1995).

Hamal, A. et al, Molecular characterisation and expression of an *Arabidopsis thaliana* L. MAP kinase cDNA, AtMAP2Kα, *Plant Science*, 140, pp. 41–52 (1999).

Mansour, S. et al., Constitutively Active Mitogen–activated Protein Kinase Kinase 1 (MAPKK1) and MAPKK2 Mediate Similar Trnascriptional and Morphological Responses, *Cell Growth and Differential*, vol. 7, pp. 243–250 (2/98).

Brunet, A. et al., Constitutively active mutants of MAP kinase kinase (MEK1) induce growth factor–relaxation and oncogenicity when expressed in fibroblasts, *Oncogenicity of Constitutively Active Map Kinase Kinase*, 9, pp. 3379–3387 (1994).

Zheng, C. et al., Activation of MEK family kinases requires phosphorylation of two conserved Ser/Thr residues, *The EMBO Journal*, vol. 13, No. 5, pp. 1123–1131 (1994).

Ligterink et al. Science, vol. 276, pp. 2054–2057, Jun. 1997.*

Linthorst et al. The Plant Cell, vol. 1, pp. 285–291, Mar. 1989.*

Bennetzen et al. Genetic Engineering, vol. 14, pp. 99–124, 1992.*

Huang et al. PNAS. USA, vol. 91, pp. 8960–8963, Sep. 1994.*

* cited by examiner

*Primary Examiner*—Phuong T. Bui
*Assistant Examiner*—Medina A. Ibrahim
(74) *Attorney, Agent, or Firm*—Thompson Hine LLP

(57) ABSTRACT

A mitogen-activated protein (MAP) kinase kinase gene, tMEK2, was isolated from tomato cv. Bonny Best. By mutagenesis, a permanently-active variant, tMEK2$^{MUT}$, was created. Both wild type tMEK2 and mutant tMEK2$^{MUT}$ were driven by a strong constitutive promoter, tCUPΔ, in a tomato protoplast transient expression system. Pathogenesis-related genes, PR1b1 and PR3, and a wound-inducible gene, ER5, were activated by tMEK2$^{MUT}$ expression revealing the convergence of the signal transduction pathways for pathogen attack and mechanical stress at the level of MAPKK. Activation of biotic and abiotic stress response genes downstream of tMEK2 occurred through divergent pathways involving at least two classes of mitogen-activated protein kinase. This study shows that tMEK2 may play an important role in the interaction of signal transduction pathways that mediate responses to both biotic (eg disease) and abiotic (wound responsiveness) stresses.

6 Claims, 11 Drawing Sheets

```
  1 ATGAAGAAAGGATCTTTTGCACCTAATCTTAAACTCTCTCTTCCTCCTCCTGATGAAGTT   60
  1  M  K  K  G  S  F  A  P  N  L  K  L  S  L  P  P  P  D  E  V    20

61 GCTCTCTCCAAATTCCTGACTGAATCAGGAACATTTAAGGATGGAGATCTTCTGGTGAAT  120
 21  A  L  S  K  F  L  T  E  S  G  T  F  K  D  G  D  L  L  V  N    40

121 AGAGATGGAGTTCGAATTGTTTCGCAGAGTGAAGTTGCAGCTCCTTCAGTTATACAGCCA  180
 41  R  D  G  V  R  I  V  S  Q  S  E  V  A  A  P  S  V  I  Q  P    60

181 TCAGACAACCAGTTATGCTTAGCTGATTTTGAAGCAGTAAAAGTTATTGGAAAGGGAAAT  240
 61  S  D  N  Q  L  C  L  A  D  F  E  A  V  K  V  I  G  K  G  N    80
                                                            I
241 GGTGGTATAGTGCGGCTGGTTCAGCATAAATGGACAGGGCAATTTTTCGCTCTCAAGGTT  300
 81  G  G  I  V  R  L  V  Q  H  K  W  T  G  Q  F  F  A  L  K  V   100
                                                            II
301 ATTCAGATGAATATTGATGAGTCTATGCGCAAACATATTGCTCAAGAACTGAGAATTAAT  360
101  I  Q  M  N  I  D  E  S  M  R  K  H  I  A  Q  E  L  R  I  N   120
                                                     III
361 CAGTCATCCCAGTGTCCATATGTTGTCATATGCTATCAGTCGTTCTTCGACAATGGTGCT  420
121  Q  S  S  Q  C  P  Y  V  V  I  C  Y  Q  S  F  F  D  N  G  A   140
                                              IV
421 ATATCCTTGATTTTGGAGTATATGGATGGTGGTTCCTTAGCAGATTTTCTGAAAAAGGTC  480
141  I  S  L  I  L  E  Y  M  D  G  G  S  L  A  D  F  L  K  K  V   160
                               V
481 AAAACAATACCTGAACGATTTCTTGCTGTTATCTGCAAACAGGTTCTCAAAGGCTTGTGG  540
161  K  T  I  P  E  R  F  L  A  V  I  C  K  Q  V  L  K  G  L  W   180
                                                          VIa
541 TATCTTCATCATGAGAAGCATATTATTCACAGGGATTTGAAACCTTCGAATTTGCTAATC  600
181  Y  L  H  H  E  K  H  I  I  H  R  D  L  K  P  S  N  L  L  I   200
                                                       VIb
601 AATCACAGAGGTGATGTCAAAATCACAGACTTTGGTGTGAGTGCAGTACTAGCAAGCACA  660
201  N  H  R  G  D  V  K  I  T  D  F  G  V  S  A  V  L  A  S  T   220
                                    VII
661 TCTGGACTGGCCAATACCTTTGTCGGCACATACAACTATATGTCTCCAGAGAGAATTTCA  720
221  S  G  L  A  N  T  F  V  G  T  Y  N  Y  M  S  P  E  R  I  S   240
                                                      VIII
721 GGAGGTGCCTATGATTACAAAAGCGACATTTGGAGCTTGGGTTTAGTCTTGCTCGAGTGT  780
241  G  G  A  Y  D  Y  K  S  D  I  W  S  L  G  L  V  L  L  E  C   260
                                        IX
781 GCAACAGGTCATTTCCCATATAAACCACCCGAGGGAGATGAAGGATGGGTCAATGTCTAT  840
261  A  T  G  H  F  P  Y  K  P  P  E  G  D  E  G  W  V  N  V  Y   280

841 GAACTTATGGAAACCATAGTTGACCAACCAGAACCTTGTGCACCTCCTGACCAATTTTCT  900
281  E  L  M  E  T  I  V  D  Q  P  E  P  C  A  P  P  D  Q  F  S   300
                                     X
901 CCACAATTCTGCTCATTCATATCTGCATGTGTCCAGAAGCACCAGAAGGACAGACTGTCG  960
301  P  Q  F  C  S  F  I  S  A  C  V  Q  K  H  Q  K  D  R  L  S   320
                                                          XI
961 GCAAATGATCTCATGAGTCACCCTTTCATCACCATGTACGATGACCAGGATATCGATCTT 1020
321  A  N  D  L  M  S  H  P  F  I  T  M  Y  D  D  Q  D  I  D  L   340

1021 GGATCTTACTTCACTTCCGCAGGACCTCCATTGGCAACACTTACTGAGCTATAA       1074
341  G  S  Y  F  T  S  A  G  P  P  L  A  T  L  T  E  L  *          358
```

FIGURE 1A

```
AtMAP2Kβ    LDMVKVIGKGSSGVVQLVQHKWTGQFFALKVIQLN-IDEAIRKAIAQELKINQSSQ-
NPK2        MRVFGAIGSGASSVVQRAIHIPTHRIIALKKINIF--EKEKRQQLLTEIRTLCEAPC
AtMKK3      MRVFGAIGSGASSVVQRAIHIPNHRILALKKINIF--EREKRQQLLTEIRTLCEAPC
DdMEK1      LKIIRVLGRGAGGVVKLAYHETSGTYIALKVITLD-IQENIRKQIILELKTLHKTS-
LPK         YSSKRNVGAGASGDVFFARLKN-GTSIALKRIPIS-SK-AHRDEVDRELQVFMARAD
HEP         LKHLGDLGNGTSGNVVKMMHLSSNTIIAVKQMRRT-GNAEENKRILMDLDVVLKSHD
MEK1        FEKISELGAGNGGVVFKVSHKPSGLVMARKLIHLE-IKPAIRNQIIRELQVLHECN-
MEK5        IRYRDTLGHGNGGTVYKAYHVPSGKILAVKVILLD-ITLELQKQIMSELEILYKCD-
MKK3        LVTISELGRGAYGVVEKVRHAQSGTIMAVKRIRAT-VNSQEQKRLLMDLDINMRTVD
PBS2        LEFLDELGHGNYGNVSKVLHKPTNVIMATKEVRLE-LDEAKFRQILMELEVLHKCN-
STE7        LVQLGKIGAGNSGTVVKALHVPDSKIVAKKTIPVEQNNSTIINQLVRELSIVKNVKP
HST7        LLTLKQLGSGNSGSVSKILHIPTQKTMAKKIIHID-SKSVIQTQIIRELRILHECH-
MKK1        IETLGILGEGAGGSVSKCKLKNGSKIFALKVINTLNTDPEYQKQIFRELQFNRSFQ-
                                                                 VIb

AtMAP2Kα    -----------------------------------------------RHIVHRDIK
AtMKK4      -----------------------------------------------RHIVHRDIK
AtMEK1      -----------------------------------------------RRIIHRDLK
LeMEK1      -----------------------------------------------KHIIHRDLK
ZmMEK1      -----------------------------------------------RHVIHRDIK
AtMAP2Kβ    CPNLVTSYQSFYDN---GAISLILEYMDGGSLADFLKSVK--------RHIIHRDLK
NPK2        CQGLVEFYGAFYTPDS-GQISIALEYMDGGSLADIIKVRK--------RHLVHRDIK
AtMKK3      HEGLVDFHGAFYSPDS-GQISIALEYMNGGSLADILKVTK--------RHLVHRDIK
DdMEK1      YPYIVSFYDAFYTE---GSIFIALEFMELGSLSDIMKKTS--------LHLIHRDIK
LPK         SPYVMNNYGAFWDAED-DAIVIPMEWMPYTVKDLGLFWGG--------KRVLHRDLK
HEP         CKYIVKCLGCFVRDP---DVWICMELMS-MCFDKLLKLSK--------HGVIHRDVK
MEK1        SPYIVGFYGAFYSD---GEISICMEHMDGGSLDQVLKKAG--------HKIMHRDVK
MEK5        SSYIIGFYGAFFVE---NRISICTEFMDGGSLDVYRKI----------LKILHRDVK
MKK3        CFYTVTFYGALFRE---GDVWICMELMDT-SLDKFYRKVLDKNM-----LSVIHRDVK
PBS2        SPYIVDFYGAFFIE---GAVYMCMEYMDGGSLDKIYDESSEIG------HNIIHRDVK
STE7        HENIITFYGAYYNQHINNEIIILMEYSDCGSLDKILSVYKRFVQRGTV-YKIIHRDIK
HST7        SPYIIEFYGACLNNNN--TIVICMEYCNCGSLDKILPLCEN--------HKIIHRDIK
MKK1        SEYIVRYYGMFTD-DENSSIYIAMEYMGGRSLDAIYKNLLERGG-----KKVIHRDIK
```

Figure 1b-1

```
                              VII                              VIII
AtMAP2Kα    PSDLLINSA-KNVKIADFGVSRILAQ TMDPCNS S-VGTIAYMSPERINTDLNHGRYDG
AtMKK4      PSNLLINSA-KNVKIADFGVSRILAQ TMDPCNS S-VGTIAYMSPERINTDLNQGKYDG
AtMEK1      PSNLLINHR-GEVKITDFGVSKILTS TSSLANS F-VGTYPYMSPERIS-----GSLYS
LeMEK1      PSNLLINHR-GDVKITDFGVSAVLAS TSGLANT F-VGTYNYMSPERIS-----GGAYD
ZmMEK1      PSNLLVNKK-GEVKITDFGVSAVLAS SIGQRDT F-VGTYNYMAPERIS-----GSTYD
AtMAP2Kβ    PSNLLINHR-GEVKITDFGVSTVMTN TAGLANT F-VGTYNYMSPERIV-----GNKYG
OsMAP2K1                              DT F-TGTYNYMAPERIS-----GQKHG
NPK2        PANLLVNRK-GEPKITDFGISAGLES SIAMCAT F-VGTVTYMSPERIRNE-----NYS
AtMKK3      PANLLINHK-GEPKITDFGISAGLEN SMAMCAT F-VGTVTYMSPERIRND-----SYS
DdMEK1      PSNILVNNK-GEAKIADFGVSGQLQH TLSKAVT W-VGTVTYMSPERIS----GRSYSF
LPK         PSNLLISET-GHVKIADFGVS-KLIQ TLAVSST Y-VATMCFMAPERLEQG-----MYG
HEP         PSNILIDER-GNIKLCDFGISGRLVD SK--ANT R-AGCAAYMAPERIDPK---KPKYD
MEK1        PSNILVNSR-GEIKLCDFGVSGQLID SM--ANS F-VGTRSYMSPERLQ----GTHYSV
MEK5        PSNMLVNTS-GQVKLCDFGVSTQLVN SI--AKT Y-VGTNAYMAPERIS-----GEQYG
MKK3        PSNVLINKE-GHVKMCDFGISGYLVD SV--AKT MDAGCKPYMAPERINPELNQK-GYN
PBS2        PTNILCSANQGTVKLCDFGVSGNLVA SL--AKT N-IGCQSYMAPERIKSLNPDRATYT
STE7        PSNVLINSK-GQIKLCDFGVSKKLIN SI--ADT F-VGTSTYMSPERIQ-----GNVYS
HST7        PNNVLMTHK-GEFKLCDFGVSRELTN SLAMADT F-VGTSMYMSPERIQ-----GLDYG
MKK1        PQNILLNEN-GQVKLCDFGVSGEAVN SL--ATT F-TGTSFYMAPERIQ-----GQPYS
                                       *    *
                IX
AtMAP2Kα    YAGDVWSLGVSILEFYLGRFPFAVSRQ--------------------------------
AtMKK4      YAGDIWSLGVSILEFYLGRFPFPVSRQ--------------------------------
AtMEK1      NKSDIWSLGLVLLECATGKFPYTPPEHKK------------------------------
LeMEK1      YKSDIWSLGLVLLECATGHFPYKPPEGDE------------------------------
ZmMEK1      YKSDIWSLGLVILECAIGRFPYIPSEGE-------------------------------
AtMAP2K     NKSDIWSLGLVVLECATGKFPYAPPNQEE------------------------------
OsMAP2K1    YMSDIWSLGLVMLELATGEFPYPPRE---------------------------------
NPK2        YPADIWSLGLALFECGTGEFPYTANE---------------------------------
AtMKK3      YPADIWSLGLALFECGTGEFPYIANE---------------------------------
DdMEK1      DSDIWSLGLTILECAIGKFPYGSNLPHQQQQPLQQQQQ-QLQNLDINNSNNNIRNSNNN
LPK         FSSDVWSLGLTMIGAVTGKNPWAPPEE--------------------------------
HEP         IRADVWSLGITLVELATARSPYEGC----------------------------------
MEK1        QSDIWSMGLSLVEMAVGRYPIPPPDAKELELMFG-CQ----------------------
MEK5        IHSDVWSLGISFMELALGRFPYPQIQKNQ------------------------------
MKK3        VKSDVWSLGITMIEMAILRFPYESWG---------------------------------
PBS2        VQSDIWSLGLSILEMALGRYPYPPE----------------------------------
STE7        IKGDVWSLGLMIIELVTGEFPLGGHN---------------------------------
HST7        VKSDVWSTGLMLIELASGV-PVWSEDDNNNDDDEDDEDD--------------------
MKK1        VTSDVWSLGLTILEVANGKFPCSSEKMAAN-----------------------------
```

Figure 1b-2

```
                                                                   X
AtMAP2Kα    ---------------------------------------GDWASLMCAICMSQPPEAPATA-
AtMKK4      ---------------------------------------GDWASLMCAICMSQPPEAPATA-
AtMEK1      ---------------------------------------GWSSVYELVDAIVENPPPCAPSNL-
LeMEK1      ---------------------------------------GWVNVYELMETIVDQPEPCAPPDQ-
ZmMEK1      ---------------------------------------GWLSFYELLEAIVDQPPPSAPADQ-
AtMAP2Kβ    ---------------------------------------TWTSVFELMEAIVDQPPPALPSGN-
OsMAP2K1    -----------------------------------------SFYELLEAVVDHPPPSAPSDQ-
NPK2        ---------------------------------------GPVNLMLQILDDPSPSLSGHE-
AtMKK3      ---------------------------------------GPVNLMLQILDDPSPTPPKQE-
DdMEK1      NNNNNNNNNNNNNNNNNNNNNVLDISNGGLVDSGSSVPEGMGFWVLLDCIVKEEVPILPS-T-
LPK         ----------------------------------------MNLYQLLGKMANGSTPTLPKSG-
HEP         ----------------------------------------NTDFEVLTKVLDSEPPCLPYGEG
MEK1        ----------------------------GMDSRPPMAIFELLDYIVNEPPPKLPSGV-

XI
AtMAP2Kα    -------SQEFRHFVSCCLQSDPPKR
AtMKK4      -------SPEFRHFISCCLQREPGKR
AtMEK1      ------FSPEFCSFISQCVQKDPRDR
LeMEK1      ------FSPQFCSFISACVQKHQKDR
ZmMEK1      ------FSPEFCSFISSCIQKDPAQR
AtMAP2Kβ    ------FSPELSSFISTCLQKEPNSR
OsMAP2K1    ------FSEEFCSFVSACIQKNASDR
NPK2        ------FSPEFCSFIDACLKKNPDDR
AtMKK3      ------FSPEFCSFIDACLQKDPDAR
DdMEK1      ------FSKEFRSFISECLQKEPTER
LPK         -----AFSDDVKDFVKQCLERDPDTR
HEP         YN----FSQQFRDFVIKCLTKNHQDR
MEK1        ------FSLEFQDFVNKCLIKNPAER
```

Figure 1b-3

| | | | |
|---|---|---|---|
| 1. tMEK2 | 214 | SAVLA*STS*GLANTF | 227 tomato cv Bonny Best |
| 2. AtMAP2K | | SRILAQ*T*MDPCN*SS* | Arabidopsis |
| 3. AtMKK4 | | SRILAQ*T*MDPCN*SS* | Arabidopsis |
| 4. AtMEK1 | | SKILT*STSS*LAN*S*F | Arabidopsis |
| 5. LeMEK1 | | SAVLA*STS*GLANTF | tomato cv Ailsa Craig |
| 6. ZmMEK1 | | SAVLA*SS*IGQRDTF | maize |
| 7. AtMAP2K | | STVM*T*N*T*AGLANTF | Arabidopsis |
| 8. NPK2 | | SAGLE*SS*IAMCATF | tobacco |
| 9. AtMKK3 | | SAGLEN*S*MAMCATF | Arabidopsis |
| 10. DdMEK1 | | SGQLQH*TLS*KAV*T*W | *D. discoideum* |
| 11. LPK | | S-KLIQ*TL*AV*SST*Y | *leishmania donovani* |
| 12. HEP | | SGRLVD*S*K-AN*T*R | *Drosophila* |
| 13. MEK1 | | SGQLID*S*M-AN*S*F | human |
| 14. MEK5 | | STQLVN*S*I-AK*T*Y | rat |
| 15. MKK3 | | SGYLVD*S*V-AK*T*M | human |
| 16. PBS2 | | SGNLVA*S*L-AK*T*N | yeast |
| 17. STE7 | | SKKLIN*S*I-AD*T*F | yeast |
| 18. HST7 | | SRELTN*S*LAMAD*T*F | *Candida albicans* |
| 19. MKK1 | | SGEAVN*S*L-A*TT*F | yeast |

FIGURE 1C

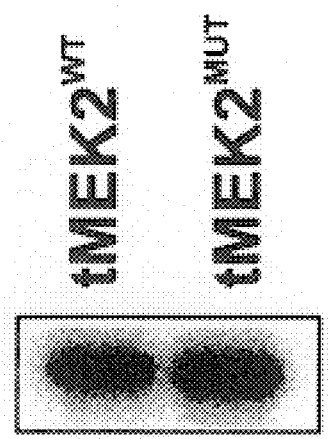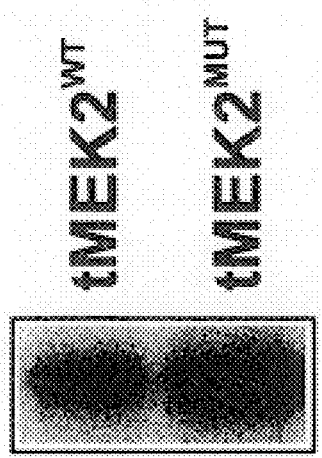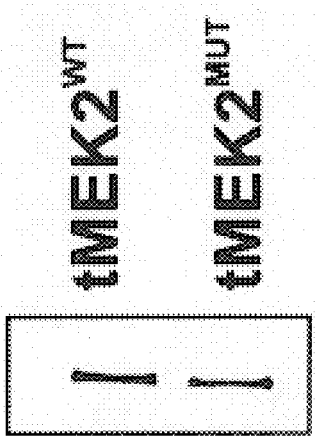
FIG. 2

CONTROL CONSTRUCT
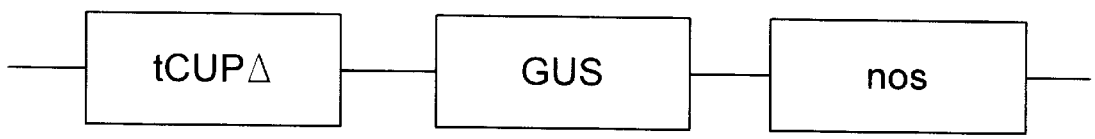
tMEK2$^{WT}$ CONSTRUCT
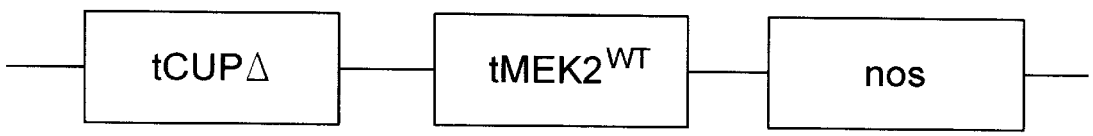
tMEK2$^{MUT}$ CONSTRUCT
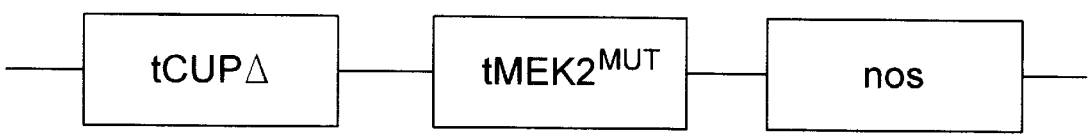
FIG. 3

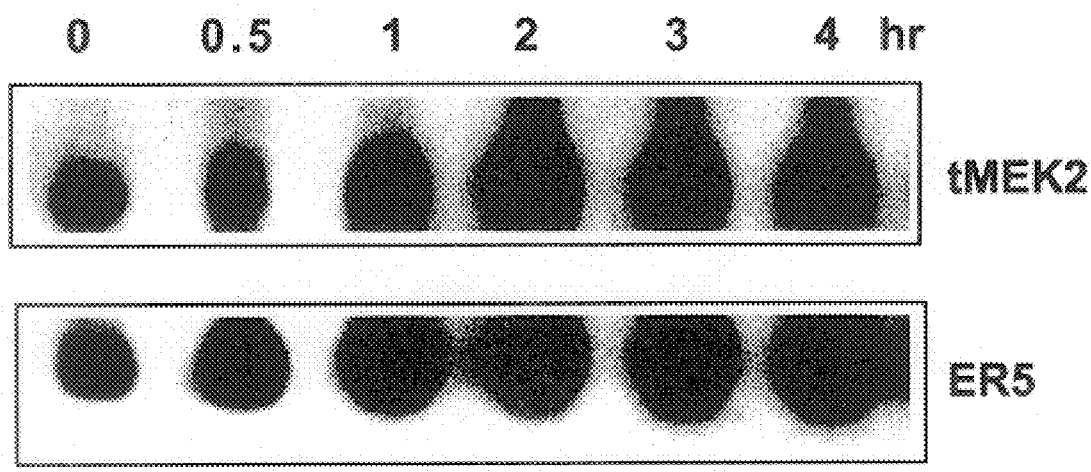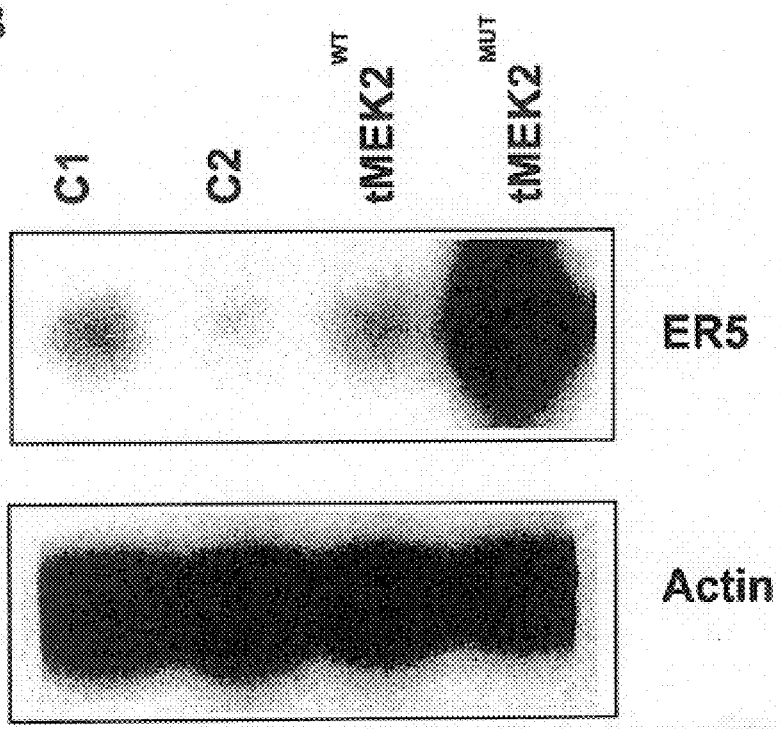
FIG. 5

PLANT-DERIVED MAP KINASE KINASE

The present invention relates to a derivative of a mitogen-activated protein (MAP) kinase kinase and the use of said derivative for increasing disease resistance and enhanced stress tolerance in plants.

BACKGROUND OF THE INVENTION

Signaling mechanisms that mediate plant defense responses may be strongly conserved among plants. This is supported by the observation that several classes of R genes confer disease resistance when expressed in heterologous plant species. For instance, the tomato disease resistance gene, Cf-9, was shown to confer responsiveness to the fungal avirulence gene product Avr9 in transgenic tobacco and potato (Hammond-Kosack et al., 1998). Although *Cladosporium fulvum* is exclusively a fungal pathogen of tomato, a rapid hypersensitive response (HR) was induced in transgenic tobacco and potato by experimentally allowing these specific interactions to occur which then induced signaling pathways that could be common to the plants. Furthermore, the tomato disease resistance gene, Pto, which specifies race-specific resistance to the bacterial pathogen *Pseudomonas syringase* pv tomato carrying the avrPto gene, also increased the resistance of tomato to *Xanthomonas campestris* pv *vesicatoria* and *Cladosporium fulvum* when over expressed (Tang et al., 1999). Clearly, it is the recognition of the pathogen that is unique to most plant species; whereas, the defense response is similar among them.

Considerable progress has now been made in understanding the signal transuction pathways following perception of biotic and abiotic stresses and the information is being used to develop strategies for modifying transgenic plants. Separate manipulations of the G protein pathway (Xing et al., 1996, 1997) may elevate pathogen resistance or induce defense reactions in transgenic tobacco (Beffa et al., 1995) and increase resistance to tobacco mosaic virus infection (Sano et al., 1994). Multiple roles for MAPK (mitogen-activated protein kinase) in plant signal transduction have also been shown, including responsiveness to pathogens, wounding and other abiotic stresses, as well as plant hormones such as ABA, auxin and ethylene (Hirt, 1997; Kovtun et al., 1998). MAPKK (mitogen-activated protein kinase kinase) from Arabidopsis (AtMEK1) and tomato (LeMEK1) have been shown to be induced by wounding (MNorris et al., 1997; Hackett et al., 1998), and the malze (ZmMEK1) gene was induced by high salinity and cold (Hardin and Wolniak, 1998). These enzymes interact within MAP kinase pathways that are extensively used for transcytoplasmic signaling to the nucleus. In the MAPK signal transduction cascade, MAPKK (MAP kinase kinase) is activated by upstream MAPKKK (mitogen-activated protein kinase kinase kinase) and in turn activates MAPK. The transcription of specific genes is induced by MAPK through phosphorylation and activation of transcription factors. This pathway has not yet been manipulated in plants.

SUMMARY OF THE INVENTION

The present invention relates to a derivative of a mitogen-activated protein (MAP) kinase kinase and the use of said derivative for increasing disease resistance and enhanced stress tolerance in plants.

According to the present invention it was determined that mutagenesis of a core phosphorylation site of a member of the MAPK cascade can create a permanently-active form, which stimulates both pathogen- and wound-inducible genes when introduced into plant cells.

Thus, according to the present invention there is provided a nucleic acid sequence encoding a derivative of a mitogen-activated protein kinase kinase gene from plants, wherein said derivative contains a negative charge in a core phosphorylation site of said protein kinase kinase gene.

Further according to the present invention there is provided a derivative of a mitogen-activated protein kinase kinase gene from plants, wherein said derivative contains a negative charge in a core phosphorylation site of said protein kinase kinase gene.

In a further embodiment of the present invention there is provided a cloning vector comprising a nucleic acid sequence encoding a derivative of a mitogen-activated protein kinase kinase gene from plants, wherein said derivative contains a negative charge in a core phosphorylation site of said protein kinase kinase gene.

The present invention also includes a transgenic plant comprising a nucleic acid sequence encoding a derivative of a mitogen-activated protein kinase kinase gene, wherein said derivative contains a negative charge in a core phosphorylation site of said protein kinase kinase gene.

Further, according to the present invention there is provided a method of increasing disease resistance or enhancing stress tolerance in a plant by introducing into said plant a nucleic acid sequence encoding a derivative of a mitogen-activated protein kinase kinase gene, wherein said derivative contains a negative charge in a core phosphorylation site of said protein kinase kinase gene.

BRIEF DESCRIPTION OF THE DRAWINGS

These and other features of the invention will become more apparent from the following description in which reference is made to the appended drawings wherein:

FIG. 1 shows sequence analysis of tMEK2.

FIG. 1a shows the DNA (SEQ ID NO:1) and deduced amino acid sequence (SEQ ID NO: 2). Roman numerals under the sequence indicate the 11 subdomains found in protein kinases. The asterisk indicates stop condon.

FIG. 1b shows the alignment of the deduced amino acid sequences from catalytic domains of MAPKK subfamily members (SEQ ID NO: 3 to 21).

FIG. 1c shows the alignment of amino acid sequences of tMEK2 with other MAPKKs between subdomain VII and VIII. Dashes represent gaps introduced for maximum matching. The amino acid residues in bold and italics between subdomain VII and VIII show putative phosphorylation sites.

FIG. 2 shows the autophosphorylation and substrate phosphorylation activity of tMED2, FIG. 2a shows the autophosphorylation of tMEK2$^{WT}$ and tMEK$^{MUT}$. Recombinant (GST-tMEK2$^{WT}$ or GST-tMEK2$^{MUT}$ proteins were incubated in vitro without any protein kinase substrate followed by SDS-PAGE and autoradiography.

FIG. 2b shows the phosphorylation of myelin basic protein (MPB) by tMEK2$^{WT}$ and tMEK$^{MUT}$. Recombinant GST-tMEK2$^{WT}$ or GST-tMEK2$^{MUT}$ proteins were incubated in vitro with MBP followed by SDS-PAGE and transfer to nitrocellulose. The upper panel is the autoradiography of he nitrocellulose filter. The lower panel is the immunoblot with anti-GST antibody.

FIG. 3 shows the constructs of tMEK2$^{WT}$ or tMEK$^{MUT}$ driven by the constitutive promoter tCUPΔ or control plasmid showing GUS gene driven by the constitutive promoter tCUPΔ.

FIG. 5 shows the activation of ER5 by tMEK2.

FIG. 5a shows RNA gel blot analysis of total RNA (15 μg) from leaves following wounding for the indicated time in hours, showing wound-induced activation of tMEK2 and ER5 genes.

FIG. 5b shows the activation of ER5 gene by tMEK2. The effect was analysed by quantitative RT-PCR following transient expression of tMED2 in protoplasts. Lane settings are as described in FIG. 4. Tomato actin was used as an internal standard.

DESCRIPTION OF PREFERRED EMBODIMENT

Figure 4:
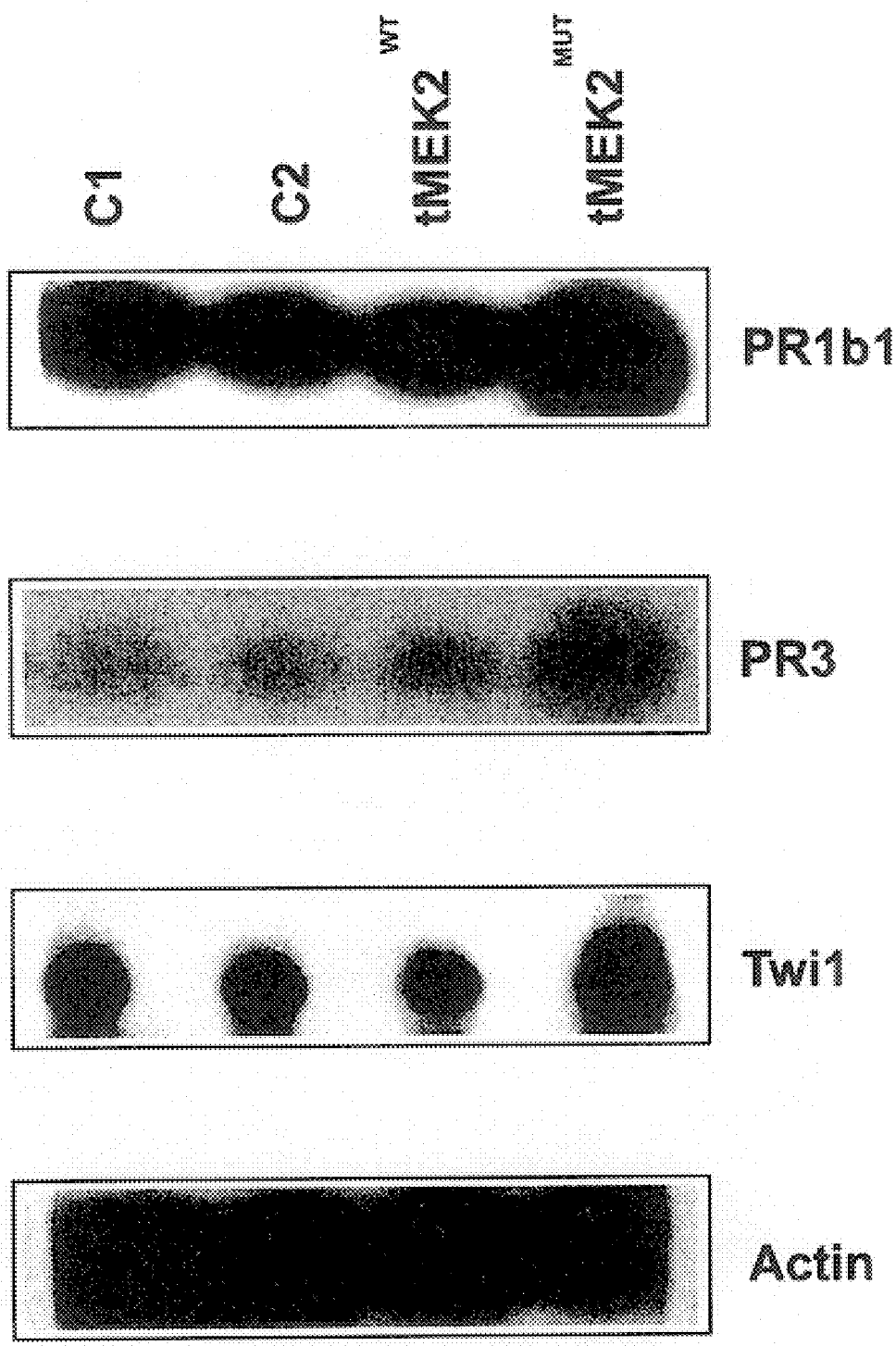
FIG. 4 shows the expression of tMEK2 in tomato leaf mesophyll protoplasts. The effect was analysed by quantitative RT-PCR following transient expression of tMED2 in protoplasts. C1, no electroporation; C2, electroporation of control plasmid; MEK2$^{WT}$, electroporation of plasmid with tMED2$^{WT}$ driven by the tCUPΔ promoter, electroporation of plasmid with tMED2$^{MUT}$ driven by tCUPΔ promoter. The pathogenesis-related genes PR1b1, PR3 and Twi1 were tested. Tomato actin was used as an internal standard.

According to the present invention there is provided a derivative of a mitogen-activated protein kinase kinase (MAPKK). The present invention also relates to a method for increasing disease resistance and enhanced stress tolerance in plants using said derivative.

When used herein the term derivative means a modified MAPKK protein, wherein said modification includes the replacement of one or more amino acids of the wild type MAPKK with one or more other amino acids. Therefore said derivative is a non-naturally occurring variant of the wild type MAPKK.

MAPK signaling cascades are ubiquitous among eukaryotes from yeast to human (Guan, 1994) and mediate a large array of signal transduction pathways in plants (Hirt, 1997; Mizoguchi et al., 1997). The cascades utilize the reversible phosphorylation of regulatory proteins to achieve rapid biochemical responses to changing external and internal stimuli. A specific MAPK is rapidly activated by pathways responding to cold, drought, mechanical stimuli and wounding (Bogre et al., 1997; Jonak et al., 1996; Seo et al., 1995; Usami et al., 1995). MAPKs are also rapidly activated by pathways responding to pathogen elicitors (Ligterink et al., 1997; Suzuki and Shinshi, 1995). Other factors such as salicyclic acid which is a signaling molecule in the pathogen response, may intervene in the signal cascade by transiently activating a MAPK in tobacco cells (Zhang and Klessig, 1997). MAPKK, which activates MAPK by phosphorylation in the signal cascade has been identified in Arabidopsis, tobacco, maize and tomato (Mizoguchi et al., 1997; Shibata et al., 1995; Hardin and Wolniak, 1998). Although phosphorylation of MAPKK by MAPKKK is the primary mechanism for initiating the signal cascade, regulation at the level of gene expression has also been implied. For instance, transcriptional activity of an Arabidopsis MAPKK, MEK1 (Morris et al., 1997), and a tomato MAPKK, tMEK1 (Hackett et al., 1998), was increased by wounding. Transcriptional activity of ZmMEK1, a maize MAPKK, was slightly increased in roots by high salinity and was substantially decreased by cold (Hardin and Wolniak, 1998). In this study, tomato tMEK2 mRNA accumulation was also induced by wounding of leaves but transient expression in protoplasts did not result in the activation of the target gene ER5. This observation supported the view that biochemical activation of MAPKK by phosphorylation was the primary factor in signal transduction and that transcriptional control plays a secondary role.

Yeast and animal MAPKK are activated when serine and serine/threonine residues in the SxAxS/T motif, located upstream of the subdomain VIII are phosphorylated by MAPKKK. The putative consensus motif for characterised plant MAPKK is a S/TxXXxxS/T signature. This motif contains two additional residues when compared with the motif SxAxS/T detected in other eukaryotes. Thus, according to the present invention the use of a plant gene encoding the MAPKK is preferred to that of the yeast and animals genes, as the plant gene provides additional sites for manipulation. The plant genes also provide additional combinations of sites that can be modified according to the present invention. Thus, according to the present invention one or multiple sites of the plant gene can be modified.

According to the present invention, by creating a negative charge around a core phosphorylation site the activation by MAPKKK was not needed for MAPKK activity.

According to the present invention possible core phosphorylation sites include: serine and/or threonine sites located upstream of the subdomain VIII.

According to the present invention to the creation of a negative charge around one of said core phosphorylation sites includes replacement of one or more amino acids with an amino acid selected from the group consisting of: any negatively charged amino acids. In one embodiment of the present invention said negatively charged amino acids include glutamic acid and aspartic acid.

In one embodiment of the present invention MAPKK gene, from various sources can be modified, as described above. As noted earlier MAPK signalling cascades are ubiquitous among eukaryotes from yeast to human. Suitable examples of a suitable gene that can be used according to the present invention include *Lycopersicum esculentum* cv Bonny Best, tMED2, together with other genes available in the art, as exemplified by the following:

*Arabidopsis thaliana*, AtMAP2Kα, (Jouannic S., Hamal A., Kreis M., Henry Y. 1996, Molecular cloning of an *Arabidopsis thaliana* MAP kinase kinase-related cDNA. Plant Physiol. 112:1397)

*A. thaliana*, AtMKK4, (Genbank accession number AB015315)

*A. thaliano*, AtMEK1, (Morris P. C., Cuerrier D., Leung L., Giraudat J. 1997, Cloning and characterisation of MEK1, an Arabidopsis gene encoding a homologue of MAP kinase kinase. Plant Mol. Biol. 35: 1057–1064)

*L. esculentum* tomato c.v. Alisa Craig, LeMEK1, (Genbank accession number AJ000728)

*Zea mais*, ZmMEK1, (Genbank accession number U83625)

*A. thaliana*, AtMAP2Kβ, (Genbank accession number AJ006871)

*N. Tabucum*, NPK2, (Shibata W., Banno H., Hirano YIK., Irie K. Machida SUC., Machida Y. 1995, A tobacco protein kinase, NPK2, has a domain homologous to a domain found in activators of mitogen-activated protein kinasis (MAPKKs). Mol. Gen. Genet. 246: 401–410)

*A. thaliana*, AtMKK3, (Genbank accession number AB015314)

D. discoideum, DdMEK1, (Nakai K., Kanehisa M. 1992, A knowledge base for predicting protein localisation sites in eukaryotic cells. Genomics 14:897–911.)

Leischmania donovani, LPK, (Li S., Wilson M E., Donelson J E. 1996, Leishmania chagasi: a gene encoding a protein kinase with a catalytic domain structurally related to MAP kinase kinase. Exp. Parasitol. 82:87–96.)

Drosophilia melanogaste, HEP, (Glise B., Bourbon H., Noselli S. Hemipterous encodes a novel Drosphilia MAP kinase kinase, required for epithelial cell sheet movement. 1995, Cell 83: 451–461.)

Homo sapiens, MEK1, (Zheng C., Guan K. 1993, Cloning and characterisation of two distinct human extracellular signal-regulated kinase activator kinases MEK1 and MEK2. J. Biol. Chem. 268: 11435–11439)

R. norvegicus, MEK5, (English J M., Vanderbilt C A., Xu X., Marcus S., Cobb M H. 1995. Isolation of MEK5 and differential expression of alternatively spliced forms. J. Biol. Chem. 270: 28897–28902.)

H. sapiens, MKK3. (Derijard B., Raingeaud J., Barrett T., Wu I H., Han J., Ulevitch R J., Davis R J. 1995, Independent human MAP kinase signal transduction pathways difined by MEK and MKK isoforms. Science 267:682–685.)

Saccharomyces cerevisiae, PBS2, (Boguslawaki G., Polazzi J O. 1987, Complete nucleotide sequence of a gene conferring polymyxin B resistance on yeast: similarity of the predictied polypeptide to protein kinases. Proc. Natl. Acad. Sci. USA 84: 5848–5852.)

S. cerevisiae, STE7, (Teague M A., Chaleff D T., Errede B. 1986, Nucleotide sequence of the yeast regulatory gene STE7 predicts a protein homologous to protein kinases. Proc. Natl. Acad. Sci. USA 83: 7371–7375.)

Candida albicans, HST 7, (Clark K L., Feldmann P J. Dignard D. 1995, Constitutive activation of the Saccharomyces cerevisiae mating response pathway by a MAP kinase kinase from Candida albicans. Mol. Gen. Genet. 249: 609–621.)

S. cerevisiae, MKK1, (Irie T., Takase MKS., Lee K S., Levin D E., Araki H., Matsumoto K., Oshima Y. 1993, MKK1 and MKK2, encoding Saccharomyces cerevisiae MAP kinase kinase homologues function in the pathway mediated by protein kinase C. Mol. Cell. Biol. 13: 3076–3083.)

In a further embodiment of the present invention putative phosphorylation activation sites are selected from the group consisting of:

Lycopersicum esculentum c.v. Bonny Best, tMEK 2: 219serine, 220threonine, 221serine and 226threonine;

Arabidopsis thaliana. AtMAP2Kα: 220threonine, 226serine and 227serine;

A. thaliana, AtMKK4: 220threonine, 226serine and 227serine;

A. thaliana, AtMEK1: 219serine, 220threonine, 221serine, 222serine and 226serine;

L. esculentum, LeMEK1: 219serine, 220threonine, 221serine and 226threonine;

Zea mais, ZmMEK1: 219serine, 220serine and 226threonine;

A. thaliana, At MAP2Kβ: 218threonine, 220threonine and 226threonine;

N. Tabucum, NPK2: 219serine, 220serine and 226threonine;

A. thaliana, AtMKK3: 220serine and 226threonine;

D. discoideum, DdMEK1, 220threonine, 222serine and 226threonine;.

Leischmania donovani, LPK: 220threonine, 224serine, 225serine and 226threonine;

Drosophila melanogaste, HEP: 220serine and 226threonine;

Homo sapiens, MEK1: 220serine and 226serine;

R. norvegicus, MEK5: 220serine and 226threonine;

H. sapiens, MKK3: 220serne and 226threonine;

Saccharomyces cerevisiae, PBS2: 220serine and 226threonine;

S. cerevisiae, STE7: 220serine and 226threonine;

Candida albicans, HST 7: 220serine and 226threonine; and

S. cerevisiae. MKK1: 220serine, 225threonine and 226threonine;

wherein the amino acid numbering system is based on the tomato gene tMEK2.

In one further embodiment of the present invention, there is provided a derivative of a mitogen-activated protein kinase kinase gene from tomato cv. Bonny Best, wherein the amino acids serine221 and threonine226 have been replaced with aspartic acid.

Methods of modifying amino acid sequences are well known in the art. In general terms two primers, one for the 3' end and one for the 5' end are used to amplify the coding region. PCR-based site-directed mutagenesis was then done using the procedure as described by Higuchi (1989). Based on the sequence of the PCR product two PCR reactions are used for its mutagenesis. In PCR reaction 1, a primer containing the appropriate base substitution was used together with the 5' primer to amplify the 5' end of the coding region. In PCR reaction 2, a further primer with the appropriate base substitution was used together with the 3' primer to amplify the 3' end of the coding region. Products from both reactions were then purified and combined for 3' extension. The resulting mutant was then amplified with the original 3' and 5' primers.

The present invention also includes a suitable cloning vector containing the nucleic acid sequence encoding the derivative of the MAPK gene for transforming suitable plant recipients to increase disease resistance and enhance stress tolerance in plants. Suitable cloning vectors include any cloning vectors, Ti plasmid-derived and standard viral vectors well known in the art.

The cloning vectors can include various regulatory elements well known in the art. For example the cloning vector of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene.

The cloning vector of the present invention can also include further enhancers, either translation or transcription enhancers, as may be required. These enhancer regions are well known to persons skilled in the art, and can include the ATG initiation condon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide resistance to chemicals such as an antibiotic such as gentamycin, hygromycin, kanamycin, or herbicides such as phosphirothycin, glyphosate, chlorsulturam and the like. Similarly, enzymes providing for production of a compound identifiable by colour change such as GUS (β-glucuronidase), or luminescence, such as luciferase are useful.

A promoter, included in the cloning vector of the present invention, can include a constitutive promoter, which will ensure continued expression of the gene. The nucleic acid sequence encoding the derivative of the MAPK gene can also be under the control of a inducible promoter. Said inducible promoter is triggered by an induction response.

Generally speaking, an inducible promoter is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods.

A constitutive promoter directs the expression of a gene throughout the various parts of a plant and continuously throughout plant development. Examples of known constitutive promoters include those derived from the CaMV 35S and Agrobacterium Ti plasmid opine synthase gene (Sanders et al., 1987) or ubiquitin (Christensen et al., 1992). Additionally the constitutive promoter described in WO 97/28268 published Aug. 7, 1997.

Also considered part of this invention are transgenic plants containing the variant of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

Besides viral cloning vectors, transformation can also be accomplished by particle bombardment using the nucleic acid sequence encoding the derivative of the MAPK gene. Bombardment is a DNA delivery technique using foreign DNA particles delivered to various plant cells, tissues and species using biolistic device such as gun powder-driven biolistic device (Dupont, Wilmington, Del.), gas-driven particle delivery system, microtargeting particle accelerator, an air gun apparatus (Daniell, 1997), helium blasting (Pateddy et al., 1997) and instruments based on electric discharge. Transformation can also be achieved by direct uptake of Agrobacterium that contained foreign DNA sequence into plants via stomato in the leaves of stem or roots (Clough et al., 1998).

A further aspect of the present invention is directed to the use of said nucleic acid sequence encoding the derivative of the MAPK gene to increase disease resistance or to enhance stress tolerance in plants. In this aspect of the invention the nucleic acid is introduced into the plant using any of the methods described above.

Pathogenesis-related (PR) proteins are intra- and extra-cellular proteins that accumulate in plant tissues or cultured cells after pathogen attack or elicitor treatment (Bowles, 1990). Using PR gene expression as a marker for the plant defence response, both PR1b1 and the chitinase gene were induced by the derivative of the MAPK gene of the present invention.

Furthermore, according to the present invention, the transcription of the tomato ER5 gene, ZG (ABA), drought and wounding (Zegzouti et al., 1997) was induced by the derivative of the MAPK gene of the present invention.

Thus, according to the present invention the derivative of the MAPK gene of the present invention can activate both pathogen- and wound-related genes.

The use of said nucleic acid sequence encoding the derivative of the MAPK gene can also be used in combination with other methods to increase disease resistance or to enhance stress tolerance in plants. These other methods could include modification of downstream components for example transcription factors and transcriptional activators. The modification of transcription factors was proven to be an effective means to improve plant stress tolerance. Overexpression of a single stress-inducible transcription factor DREB1A isolated from Arabidopsis improved plant drought, salt, and freezing tolerance (Masuga et al., 1999). Overexpression of CBF1, an Arabidopsis transcriptional activator, enhanced freezing tolerance (Jaglo-Ottosen et al., 1998). There is potential that modification of transcription factors or transcriptional activators downstream of MAPK is our system will enhance disease resistance and stress tolerance.

In addition there are some parallel pathways that could contribute to increase disease resistance or to enhanced stress tolerance in plants if used in combination with the modified MAPK pathway of the present invention. An example of another parallel pathway would be calcium dependent protein kinase (CDPK) (Sheen, 1996). CPDK has also been shown to act as a key mediator for cold, salt, drought, dark and ABA stresses. In addition CDPK is involved in primary defence response to pathogen attack. Overexpression of either of two different CDPKs (ATCDPK1 and ATCDPK1a) in maize protoplasts active stress signalling (Sheen, 1996). Thus the co-manipulation of the two pathways should further strengthen the defence ability of the plant.

The present invention is illustrated by the following examples, which are not to be construed as limiting.

EXAMPLES

Example 1

Isolation and Modification of tMEK2

RNA was extracted with Extact-A-Plant™ RNA Isolation Kit (CloneTech Laboratories, Inc.) from four-week-old tomato leaves. Reverse transcription was as described in Sambrook et al. (1989). Cloning was carried out by PCR using Taq DNA polymerase (Life Technologies Inc.). A MAPKK gene, tMEK2, was isolated from tomato cv. Bonny Best by PCR (FIG. 1a) using published MAPKK gene sequences of tomato cv. Ailsa Craig and other plant species. It shares a high level of sequence homology with MAPKKs from other species and tomato cultivars (FIG. 1b) but compared with MAPKKs from mammals and yeast, tMEK2 and other plant MAPKKs have two more potential core phosphorylation sites between subdomains VII and VIII (FIG. 1c).

Using PCR-assisted, site-directed mutagenesis, amino acids serine221 and threonine226 were replaced with aspartic acid (FIG. 1c) creating a negative charge around the core phosphorylation site so that phosphorylation of MAPKK by upstream MAPKKK is no longer necessary for activity. Two primers (5'-end and 3'-end) that span the coding region of tomato cv Ailsa Craig LeMEK1 were used for the amplification of the MAPKK coding sequence in tomato cv Bonney Best. PCR-based site-directed mutagenesis was carried out as described before (Higuchi, 1989). Based on the sequence of the PCR product, two PCR reactions were run for its mutagenesis. In PCR reaction 1, a primer containing the base substitutions (5'GTATGTGCCGACAAA GTCATTGGCCAGTCCA TCTGTGCTTGCTAGTACTGCACTCACAC3', SEQ ID NO: 22) was used together with 5'-end primer to amplify a 692 bp fragment corresponding to the 5' region of the cloned MAPKK. In PCR reaction 2, a primer containing the base substitutions (5'GTACTAGCAAGCACA GATGGACTGGCCA AT GACTTTGTCGGCACATACAACTATATGTC3', SEQ ID NO: 23) was used together with 3'-end primer to amplify a 429 bp fragment corresponding to the 3' region of the cloned MAPKK. Products from PCR reaction 1 and 2 were then purified and combined for 3' extension. Mutant tMEK2 was amplified with the original 5'-end primer containing BamHI and NcoI restriction sites, and 3'-end primer containing SalI and SmaI restriction sites. The wild type and mutagenized PCR products were purified from an agarose gel using Elu-Quik DNA Purification Kit (Schleicher & Schuell) and ligated into pre-digested pGEM-T Easy vector. The inserts were digested using NcoI/SmaI and ligated into pTZ19 tCUPΔ-GUS-nos3'. This derivative of tCUP promoter was created by the following modifications to the original tCUP: mutation of the sequence, 3' deletion of the sequence, nucleotide addition to the sequence, deletion of an upstream out-of-frame ATG methionine initiator codon from the sequence, deletion of the fusion protein encoded by the tobacco genomic DNA from the sequence, addition of restriction sites to the sequence. In detail, exact nucleotide changes are (numbered relative to the tCUP sequence or to the tCUPΔ (sequence as noted): 2084 CATATGA 2090 (NdeI recognition site beginning at 2084 underlined) in the tCUP sequence mutated to 2084 CATAGATCT 2092 (BglII recognition site beginning at 2087 underlined) in the tCUPΔ sequence deleting one restriction site and one upstream out-of-frame ATG methionine initiator codon while adding another restriction site and two nucleotides: 2171 AATA- CATGG 2179 in the tCUP sequence mutated to 2173 CCACCATGG 2181 in the tCUPΔ sequence adding a Kozak consensus motif for translational initiation and an NcoI recognition site at 2176 (underlined): 2181 to 2224 (relative to tCUP sequence) of tobacco genomic DNA removed from tCUPΔ (2183 to 2226 relative to tCUPΔ), deleting the 3' end of the tCUP sequence and the N-terminal fusion peptide encoded by the tobacco genomic DNA. The tCUPΔ-GUS-nos construct was created by fusion of the tCUPΔ sequence with a GUS gene and nos terminator having the sequence 2183 CTCTAGAGGAT CCCCGGGTGGTCAGTCCCTT 2213 3' (SEQ ID NO: 24) to the GUS ATG at 2214 on the tCUPΔ sequence (see FIG. 3).

Example 2

Expression and Phosphorylation Analysis of Recombinant tMEK2

For in-frame cloning with GST into the BamHI/SalI sites in the pGEX-4T-3 vector (Amersham Pharmacia), subcloned PCR products in pGEM-T Easy vector were digested by BamHI/SalI and ligated into pGEX-4T-3 cut with the same enzymes. Sequences of cloned products were confirmed by DNA sequencing. The proteins were expressed as glutathione-S-transferase fusions (GST) and purified by glutathione-agarose (Sigma) affinity chromatography essentially as described in manufacturer's protocol. Protein concentration was determined with a Bio-Rad detection system (Bio-Rad).

Autophosphorylation assay contained 1 μg of GST-tMEK2$^{WT}$ or GST-tMEK2$^{MUT}$ in 30 mM Hepes (pH 7.5), 5 mM of MgSO$_4$, 5 mM of MnSO$_4$, and 1 mM CaCl$_2$, 10 mM ATP, and 3 μCi γ-$^{32}$P-ATP (specific activity 222 TBq/mmol) in a total volume of 15 μl. The reaction mixture was incubated at 30° C. for 45 min and the reaction was stopped by boiling 3 min in SDS sample buffer. As shown in FIG. 2a, both wild type and mutant forms of the tMEK2 enzyme showed autophosphorylation activity.

Substrate phosphorylation assays contained 1 μg of GST-tMEK2$^{WT}$ or GST-tMEK2$^{MUT}$, 2 μg of myelin basic protein (MBP, Life Technologies Inc.), 30 mM Hepes (pH 7.5), 5 mM MgSO$_4$ and 5 mM MnSO$_4$. Reactions were carried out at 30° C. for 30 min. Phosphorylated products were separated by 10% SDS-PAGE, transferred to nitrocellulose and autoradiographed. Both the wild type and mutant forms of the tMEK2 enzyme phosphorylated myelin basic protein (MPB) in vitro (FIG. 2b). Protein immunoblotting was performed as described previously (Xing et al., 1996) using antiGST antibody (Amershan Pharmacia) and alkaline phosphatase-conjugated secondary antibody.

Example 3

Activation of Pathogen- and Wound-related Genes by tMEK2

To examine the effects of tMEK2$^{WT}$ and tMEK2$^{MUT}$ on the activation of pathogenesis-related (PR) or other pathogen-inducible genes a tomato protoplast transient expression system was developed. Chimeric genes, tCUPΔ-tMEK2$^{WT}$-nos and tCUPΔ-tMEK2$^{MUT}$-nos, were constructed using the storing constitutive promoter, tCUPΔ, which was derived from the tCUP promoter as by modification of the mRNA leader sequence described above. After electroporation, transient expression of potential target genes was detected by quantitative RT-PCR. The genes analysed included PR1b1, which is activated by tomato mosaic virus (Tornero et al., 1997); PR3 (chitinase), which is activated during an incompatible C. fulvam-tomato interaction (Danhash et al., 1993); and Twi, which is a pathogen- and would-inducible gene recently identified in tomato (O'Donnell, et al., 1998).

The following procedures were used.

Protoplast isolation and transformation

Tomato (*Lycopersicon esculentum* cv Bonny Best) were grown at 80% relative humidity in peat soil in growth cabinets programmed for 16 hr days at 25° C. and 8 hr nights at 22° C. Light intensity was controlled at 25 pE m-2 S-1 emitted from "cool white" fluorescent lamps (Philip Canada, Scarborough, Ontario). The youngest fully expanded leaves were surface sterilized for 5 min in 4% sodium hypochlorite and rinsed three times with sterile water. The lower epidermis was gently rubbed with Carborundum, rinsed with sterile water and leaf fragments of ca. 1 cm$^2$ were floated with exposed surface facing an enzyme solution containing 0.15% macerozyme $R_{10}$ (Yakult Honsha Co., Japan), 0.3% Cellulase "Onozuka" Rio (Yakult Honsha Co., Japan), 0.4 M sucrose in K3 medium (Maliga et. al., 1973). After overnight incubation at 30° C., the enzyme-protoplast mixture was filtered through a 100 μm nylon sieve, centrifuged at 500 g for 5 min. and floated protoplasts were collected and washed twice with W5 medium (Maliga et.al., 1973). The protoplasts were kept on ice in W5 medium for 2 hr before transformation.

The protoplasts were resuspended in electroporation buffer containing 150 mM $MgCl_2$ and 0.4 M mannitol at a density of $1 \times 10^6$ protoplasts/ml and co-electroporated with 12–15 g of pTZ19 carrying tMEK2 gene and pJD300 carrying luciferase gene in a total volume of 500 μl as described by Leckie (1994) with some modifications. Electroporation was performed at 200 volts and 100 μF (Gene Pulser II, Bio-Rad). Protoplasts were then allowed to recover on ice in the dark for 10 min followed by centrifugation at 500 g for 5 min. After removal of the supernatant, the protoplast pellet, with about 500 μl of buffer, was supplemented with another 500 μl protoplast incubation buffer. Protoplasts were incubated in the dark at 30° C. for 24 hr.

Kinase inhibitors (CalBiochem, San Diego, Calif.) at the concentration of 1 μM for staurosporine, 350 nM for SB 202190 and 1 μM for PD 98059, SB 203580 and SB 202474, when applicable, were included in the protoplast incubation buffer. The inhibitors did not change protoplast viability (data not shown).

Luciferase assay

Luciferase activity in protoplasts co-electroporated with the constructs under study and luciferase DNA as an internal control were determined for evaluation of transformation efficiency. Protoplasts were lysed in 200 μL of LUC extraction buffer (100 mM $KPO_4$, 1 mM EDTA, 10% glycerol, 0.5% Triton X-100 and 7 mM β-merceptoethanol, pH 7.8). After microfuge centrifugation, the supernatant was collected and a 200 μL aliquot of LUC assay buffer (25 mM Tricine, 15 mM $MgCl_2$, 5 mM ATP, BSA 1 mg/ml, and 5 μl β-merceptoethanol, pH 7.8) was added to each 20 μL aliquot followed by 100 μL of luciferin (0.5 mM) as substrate. The reaction was assayed in a luminometer as described (Matthews et.al., 1995).

Quantitative RT-PCR

RT-PCR was as described above. The number of PCR cycles corresponded to the high end of the range in which a linear increase in products could be detected (generally 14–16 cycles were used). Reaction products were separated on 1.0% agarose gels. Southern blot analysis was used to estimate levels of specific amplified products. Equivalence of cDNA in different samples was verified using PCR reactions for actin. Primers were designed for PCR according to published sequences for tomato PR-lbl, chitinase, Twit, ER5 and actin (Tornero et al., 1997; Danhash et al., 1993; O'Donnell et al., 1998; Zegzoutti et al. 1997; Moniz de Sa and Drouin, 1996).

Our results indicated that tomato PRlbl, chitinase and Twil genes were activated by tMEK2$^{MUT}$. This indicates that tMEK2 can mediate both pathogen and wound signals. Transient expression of the native tMEK2$^{WT}$ gene had no effect on the expression of the three target genes (FIG. 4), indicating that it is not errantly activated in the protoplast system.

Example 4

Induction of the Wound-inducible Gene ER5

Since MAPK may be the point of convergence of the signal transduction pathways for fungal elicitors and mechanical stress (Romeis et al., 1999) we also examined the induction of the wound-inducible gene, ER5 (Zegzouti et al., 1997). Wounding was carried out by crushing leaves across the lamina and mid-vein using a blunt forceps. RNA was extracted after wounding for the indicated period of time. Fifteen μg of RNA was separated per lane on a denaturing formaldehyde gel. Following transfer to nylon membranes, the blot was hybridized with radio labeled fragment of tMEK2 coding region or fragment of ER5 coding region. Autoradiography was applied to visualize the hybridization signals (Sambrook et al., 1989).

Wounding of tomato leaves induced both resident tMEK2 and ER5 genes. mRNA accumulation was detectable in 30 min and lasted for at least 4 hrs (FIG. 5a). Transient expression of the mutant tMEK2$^{MUT}$ gene in tomato protoplasts also activated ER5 (FIG. 5b); however, tMEK2$^{WT}$ did not (FIG. 5b), showing that elevated transcription of tMEK2 alone was not sufficient for transmitting the wound signal to ER5.

Example 5

Different MAPKs Downstream of tMEK2

Figure 6:
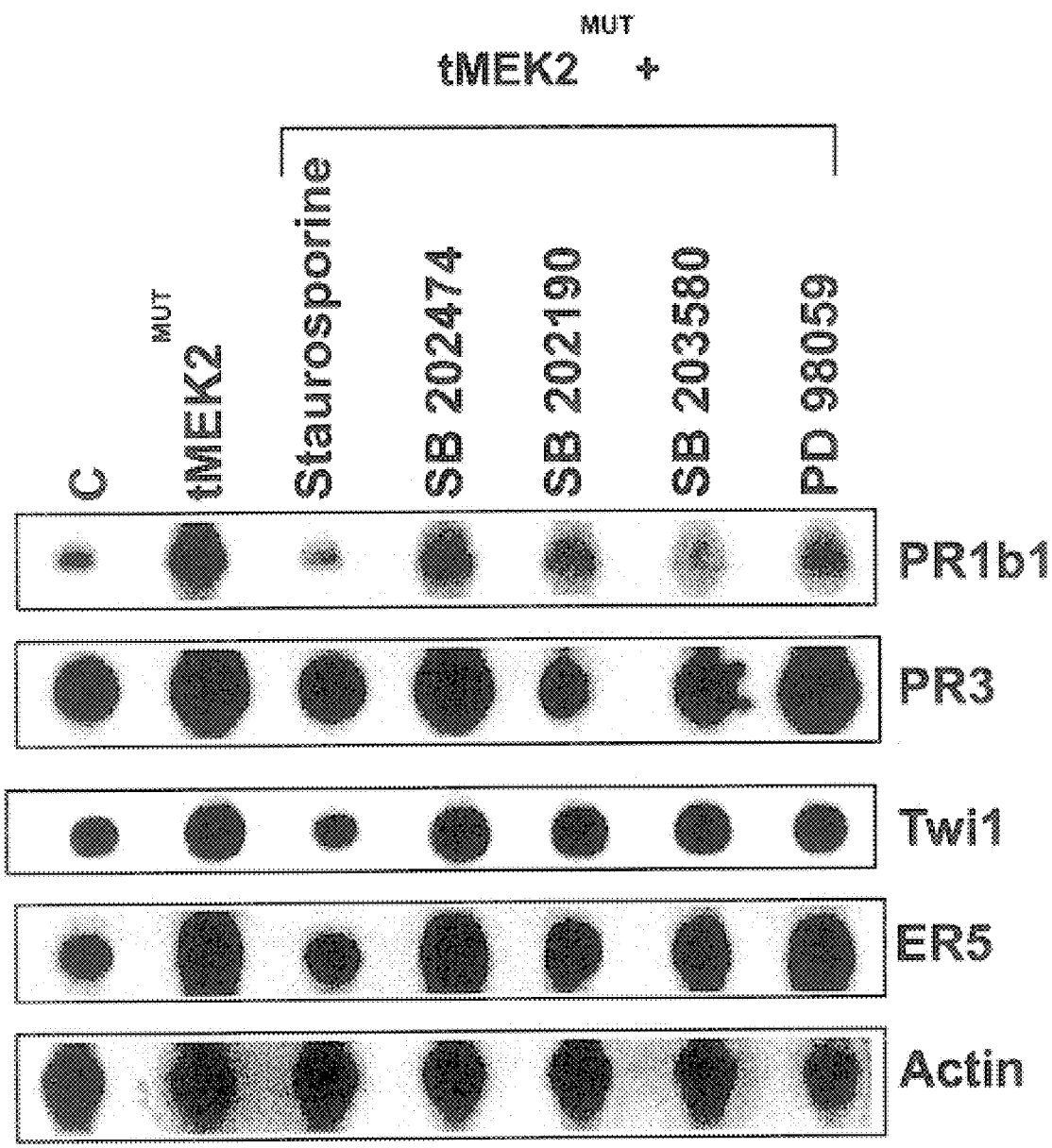
FIG. 6 shows the effect of MAPK inhibitors on tMED2$^{MUT}$-induced gene activation. Kinase inhibitors at the concentration of 1 μM for staurosporine, 350 nM for SB 202190 and 1 μM for PD 98059, SB 203580 and SB 202474 were included in the proteoplast incubation buffer.

To study divergence of the signal pathways downstream of tMEK2 the influence of tMAPK2$^{MUT}$ expression in tomato protoplasts was examined in the presence of a broad protein kinase inhibitor (staurosporine) and inhibitors specific to the p38 class MAPK (SB 202190 or SB 203580). Staurosporine inhibited all four genes that were previously activated by tMEK2$^{MUT}$; whereas, inhibitors of p38 class MAPK inhibited the PR3 and ER5 genes but not PRlbl or Twi1. Furthermore, no effects were observed with SB202474, an inert compound acting as a negative control for MAP kinase inhibition studies, or PD 98059, an inhibitor of the MAP kinase cascade which binds to MAPKKK at a site that blocks access to activating enzymes (Alessi et al., 1995). The results, shown in FIG. 6, are consistent with the divergence of signal pathway downstream of tMEK2. One of these pathways could include a p38 class MAPK.

Example 6

Disease Resistance

Figure 7:
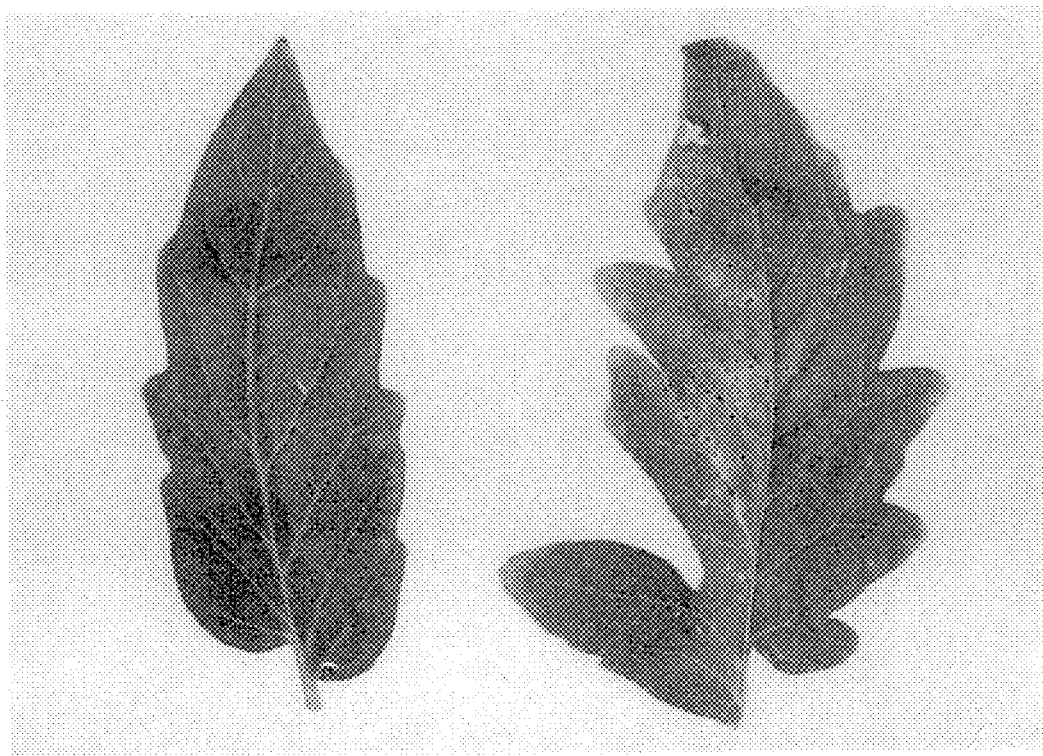
FIG. 7 shows the comparison of disease symptoms ona leaf from a wild type plant and on a leaf from tMEK2$^{MUT}$ transformed plant.

Tomato bacterial pathogen *Pseudomonas syringae* pv tomato was infiltrated into tomato leaves and the effect of inoculation was recorded 7 days after inoculation. A representative comparison of disease symptoms on a leaf from a wild-type plant and on a leaf from tMEK2$^{MUT}$ transformed plant is shown in FIG. 7.

REFERENCES

Alessi, D. R., Cuenda, A., Cohen, P., Dudley, D. T. and Saltiel, A. R. (1995) PD 098059 is a specific inhibitor of the activation of mitogen-activated protein kinase kinase in vitro and in vivo. *J. Biol. Chem.* 270, 27489–27494.

Beffa, R., Szell, M., Menwly, P., Pay, A., Vogeli-Lange, R., Metraux, J. P., Meins, F. and Nagy, F. 1995. Cholera toxin elevates pathogen resistance and induces defense reactions in transgenic tobacco plants. *EMBO Journal* 14, 5753–5761.

Bogre, L., Zwerger, K., Meskiene, I., Binarova, P., Csizmadia, V., Planck, C., Wagner, E., Hirt, H. and Heberle-Bors, E. (1997) The cdc2Ms kinase is differently regulated in the cytoplasm and the nucleus. *Plant Physiol.* 113, 841–852.

Bowles, D. J. (1990) Defense-related proteins in higher plants. *Annul Rev. Biochem.* 59, 873907.

Christensen A H., Sharrock R. A., Quail P H. 1992. Maize polyubiquitin genens: Structure, thermal perturbation of expression and transcript splicing, and promoter activity following transfer to protoplasts by electroporation. Plant Mol. Biol. 18, 675–689.

Clough S J. Bent A F. 1998. Floral dip: a simplified method for Agrobacterium-mediated transformation of Arabidopsis thaliana. Plant J. 16, 735–743.

Danhash, N., Wagemakers, C. A., van Kan, J. A. and De Wit, P. J. (1993) Molecular characterization of four chitinase cDNAs obtained from cladosporium fulvum-infected tomato. *Plant Mol. Biol.* 22, 1017–1029.

Daniell H. 1997. Transformation and foreign gene expression in plants mediated by microprojectile bombardment. Methods in Mol. Biol. 62 Recombinant Gene Expression Protocols (Tuan R., Ed), Humana Press Inc. Totowa, N.J.

Guan, K. L. (1994) The nitrogen activated protein kinase signal transduction pathway: From the cell surface to the nucleus. *Cell. Signal.* 6, 581–589.

Hackett, R. M., Oh, S. A., Morris, P. C. and Grierson, D. (1998) A tomato MAP kinase kinase gene (Accession No AJ000728) differentially regulated during fruit development, leaf senescence and wounding (PGR98-151). *Plant Physiol.* 117, 1526–1526.

Hammond-Kosack, K. E., Tang, S., Harrison, K. and Jones J. D. G. (1998) The tomato Cf-9 disease resistance gene functions in tobacco and potato to confer responsiveness to the fungal avirulence eene Product Avr9. *Plant Cell* 10, 1251–1266.

Hardin, S. C. and Wolniak, S. M. (1998) Molecular cloning and characterization of maize ZmMEK1, a protein kinase with a catalytic domain homologous to mitogen- and streeactivated protein kinase kineses. *Planta* 206, 577–584.

Higuchi, R. (1989) Using PCR to engineer DNA. In: PCR Technology: Principles and Applications for DNA Amplification (ea. Erlich HA). Stockton Press, New York.

Hirt, H. (1997) Multiple roles of MAP kineses in plant signal transduction. *Trends Plant Sci.* 2, 11–15.

Jaglo-Ottosen K R., Gilmour S J., Zarka D G., Schabenberger O., Thomashow M F. 1998. Arabidopsis CBF1 overexpression induced COR genes and enhances freezing tolerance. Science 280, 104–106.

Jonak, C., Kiegerl, S., Ligterink, W., Barker, P. J., Huskisson, N. S. and Hirt, H. (1996) Stress signaling in plants: A mitoegen-activated protein kinase pathway is activated by cold and drought. *Proc. Natl. Acad. Sci. USA* 93, 11274–11279.

Kasuga M., Liu Q., Miura S., Yamaguchi-Shinozaki K., and Shinozaki K. 1999, Improving plant drought, salt, and freezing tolerance by gene transfer of a single stress-inducible transcription factor. Nature Biotechnology 17, 287–291.

Kovtun, Y., Chiu, W-L., Zeng W. and Sheen J. (1998) Suppression of auxin signal transduction by a MAPK cascade in higher plants. Nature 395, 716–720.

Ligterink, W., Kroj, T., Nieden, U. Z., Hirt, H. and Scheel D. (1997) Receptor-mediated activation of a MAP kinase in pathogen defense of plants. *Science* 276, 2054–2057.

Maliga, P. S., Breznovitis, A. and Marton, L. (1973) Streptomycin-resistant plants from callus culture of haploid tobacco. *New Biol.* 244, 29–30.

Matthews, B. F., Saunders, J. A., GeLhardt, J. S., Lin, J. J. and Koehle, S. M. (1995) Reporter genes and transient assays for plants. *Methods Mol. Biol.* 55, 147–162.

Mizoguchi, T., Ichimura, K., and Shinozaki, K. (1997) Environmental stress response in plants: the role of mitogen-activated protein kineses. *Trends Biotech.* 15, 15–19.

Moniz de Sal, M., and Drouin, G. (1996) Phylogeny and substitution rates of angiosperm actin genes. *Mol. Biol. Evol.* 13, 1198–1212.

Morris, P. C., Guerrier, D., Leung, J., and Giraudat J. (1997) Cloning and characterisation of MEK1, an Aarabidopsis gene encoding a homologue of MAP kinase kinase. *Plant Mol. Biol.* 35, 1057–1064.

O'Donnell, P J., Truesdale, M. R., Calvert, C. M., Dorans, A., Roberts, M. R., and Bowles, D. J. (1998) A novel tomato gene that rapidly responds to wound- and pathogenrelated signals. *Plant J.* 14, 137–142.

Pareddy D., Petolino J., Skokut T., Hopkins N., Miller M., Welter M., Smith K., Clayton D., Pescitelli S., Gould A. 1997. Maize transformation via helium blasting. Maydica 42, 143–154.

Romeis, T., Piedras, P., Zhang, S., Klessig, D., Hirt, H., and Jones, J. D. G. (1999) Rapid Avr9- and Cf-9-dependent activation of MAP kineses in tobacco cell cultures and leaves: convergence of resistance gene, elicitor, wound, and salicylate responses. *Plant Cell II,* 273287.

Sambrook, J., Fristch, E. F., and Maniatis, T. (1989) Molecular Cloning: a Laboratory Manual, 2nd edn. Cold Spring Harbor, N.Y.: Cold Spring Harbor Laboratory Press.

Saunder, P. R., Winter, J. A., Barnason, A. R., Rogers, S. G., Fraley, R. T. (1987). Comparison of cauliflower mosaic virus 35S and noplaline synthase promoters in transgenic plants. *Nucleic Acids Res.* 25, 15, 1543–1558.

Sano, H., Seo, S., Orudgev, E., Youssefian, S., Ishizuka, K., and Ohashi, Y. (1994) Expression of the gene for a small GTP binding protein in transgenic tobacco elevates endogenous cytokinin levels, abnormally induces salicylic acid in response to wounding and increases resistance to tobacco mosaic virus infection. *Proc. Natl. Acad. Sci.* 91, 1055610560.

Seo, S., Okamoto, M., Seto, H., Ishizaka, K., Sano, H., and Ohashi, Y. (1995) Tobacco MAP kinase: a possible mediator in wound signal transduction pathways. *Science* 270, 19881992.

Sheen, J. (1996) Ca2+-Dependent Protein Kinases and Stress Signal Transduction in plants. *Science* 274, 1900–1902.

Shihata, W., Banno H., Ito Y., Hirano K., Irie K., Usami S., Machida C., and Machida, Y. (1995) A tobacco protein kinase, NPK2, has a domain homologous to a domain found in activators of mitogen-activated protein kineses (MAPKKs). *Mol. Gen. Genet.* 246, 401–410.

Suzuki, K., and Shinshi, H. (1995) Transient activation and tyronise phosphorylation of a protein kinase in tobacco cells treated with a fungal elicitor. *Plant Cell* 7, 639–647.

Tang, X., Xie, M., Kin, Y. J., Zhou, J., Klessig, D. F., and Martin, G. B. (1999) Overexpression of Pto activates defense responses and confers broad resistance. *Plant Cell* 11, 15–29.

Teague, M. A., Chaleff, D. T., and Errede, B. (1986) Nucleotide sequence of the yeast regulatory gene STE7 predicts a protein homologous to protein kineses. *Proc. Natl. Acad. Sci. USA* 83, 7371–7375.

Tornero, P., Gadea, J., Coejero, V., and Vera, P. (1997) Two PR-1 genes from tomato are differentially regulated and reveal a novel mode of expression of a pathogenesis-related gene during the hypersensitive response and development. Mol. Plant-Microbe Interact. 10, 624634.

Usami S., Banno H., Ito Y., Nishiha-na R., Machida Y. (1995) Cutting activates a 46-kilodalton protein kinase in plants. *Proc. Natl. Acad. Sci. USA* 92, 8660–8664.

Xing, T., Higgins, V. J., Blumwald, E. (1996) Regulation of plant defense responses to fungal pathogens: two types of protein kineses in the reversible phosphorylation of the hostplasma membrane H$^+$-ATPase. *Plant Cell* 8, 555–564.

Xing, T., Higgins, V. J., and Blumwald, E. (1997) Identification of G proteins in mediating elicitor-induced dephosphorylation of plasma membrane H$^+$-ATPase in host plant. *J. Exp. Bot.* 48, 229–238.

Zegzouti, H., Jones, B., Marty, C., Lelievre, J-M., Latché, A., Pech, J-C., and Bonzayen, M. (1997) ER5, a tomato cDNA encoding an ethylene-responsive LEA-like protein: characterization and expression in response to drought, ABA and wounding. *Plant Mol. Biol.* 35, 847–854.

Zhang, S., and Klessig, D. F. (1997) Salicylic acid activates a 48-kD MAP kinase in tobacco. *Plant Cell* 9, 809–824.

Zheng, C. F., and Guan, K. L. (1993) Cloning and characterization of two distinct human extracellular signal-regulated kinase activator kineses MEK1 and MEK2. *J. Biol. Chem.* 268, 11435–11439.

Zheng, C. F., and Guan, K. L. (1994) Activation of MEK family kineses requires phosphorylation of two conserved Ser/Thr residues. *EMBO J* 13, 1123–1131.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

The embodiments of the invention in which an exclusive property of privilege is claimed are defined as follows:

1. An isolated nucleic acid molecule comprising a nucleic acid sequence encoding a plant mitogen-activated protein kinase kinase of SEQ ID NO:2, wherein amino acids serine221 and threonine226 have been replaced with aspartic acid.

2. A cloning vector comprising the nucleic acid molecule of claim 1.

3. A transgenic plant comprising the cloning vector of claim 2.

4. A transgenic plant comprising the nucleic acid molecule of claim 1.

5. A method of increasing disease resistance in a plant by: preparing a nucleic acid molecule comprising a nucleic acid sequence encoding a plant mitogen-activated protein kinase kinase of SEQ ID NO:2, wherein amino acids serine221 and threonine226 have been replaced with aspartic acid; and introducing said nucleic acid molecule into a plant; and wherein said protein kinase kinase is expressed to a level which induces increased disease resistance in said plant.

6. A method of enhancing stress tolerance in a plant by: preparing a nucleic acid molecule comprising a nucleic acid sequence encoding a plant mitogen-activated protein kinase kinase of SEQ ID NO:2, wherein amino acids serine221 and threonine226 have been replaced with aspartic acid; and introducing said nucleic acid molecule into a plant; and wherein said protein kinase kinase is expressed to a level which induces enhanced stress tolerance in said plant.

* * * * *

SEQUENCE LISTING

<160> NUMBER OF SEQ ID NOS: 24

<210> SEQ ID NO 1
<211> LENGTH: 1074
<212> TYPE: DNA
<213> ORGANISM: Lycopersicon esculentum
<220> FEATURE:
<221> NAME/KEY: CDS
<222> LOCATION: (1)..(1074)

<400> SEQUENCE: 1

```
atg aag aaa gga tct ttt gca cct aat ctt aaa ctc tct ctt cct cct      48
Met Lys Lys Gly Ser Phe Ala Pro Asn Leu Lys Leu Ser Leu Pro Pro
 1               5                  10                  15 cct gat gaa gtt gct ctc tcc aaa ttc ctg act gaa tca gga aca ttt      96
Pro Asp Glu Val Ala Leu Ser Lys Phe Leu Thr Glu Ser Gly Thr Phe
                20                  25                  30 aag gat gga gat ctt ctg gtg aat aga gat gga gtt cga att gtt tcg     144
Lys Asp Gly Asp Leu Leu Val Asn Arg Asp Gly Val Arg Ile Val Ser
            35                  40                  45 cag agt gaa gtt gca gct cct tca gtt ata cag cca tca gac aac cag     192
Gln Ser Glu Val Ala Ala Pro Ser Val Ile Gln Pro Ser Asp Asn Gln
        50                  55                  60 tta tgc tta gct gat ttt gaa gca gta aaa gtt att gga aag gga aat     240
Leu Cys Leu Ala Asp Phe Glu Ala Val Lys Val Ile Gly Lys Gly Asn
 65                  70                  75                  80 ggt ggt ata gtg cgg ctg gtt cag cat aaa tgg aca ggg caa ttt ttc     288
Gly Gly Ile Val Arg Leu Val Gln His Lys Trp Thr Gly Gln Phe Phe
                85                  90                  95 gct ctc aag gtt att cag atg aat att gat gag tct atg cgc aaa cat     336
Ala Leu Lys Val Ile Gln Met Asn Ile Asp Glu Ser Met Arg Lys His
               100                 105                 110 att gct caa gaa ctg aga att aat cag tca tcc cag tgt cca tat gtt     384
Ile Ala Gln Glu Leu Arg Ile Asn Gln Ser Ser Gln Cys Pro Tyr Val
           115                 120                 125 gtc ata tgc tat cag tcg ttc ttc gac aat ggt gct ata tcc ttg att     432
Val Ile Cys Tyr Gln Ser Phe Phe Asp Asn Gly Ala Ile Ser Leu Ile
```

```
                130                 135                 140
ttg gag tat atg gat ggt ggt tcc tta gca gat ttt ctg aaa aag gtc      480
Leu Glu Tyr Met Asp Gly Gly Ser Leu Ala Asp Phe Leu Lys Lys Val
145                 150                 155                 160 aaa aca ata cct gaa cga ttt ctt gct gtt atc tgc aaa cag gtt ctc      528
Lys Thr Ile Pro Glu Arg Phe Leu Ala Val Ile Cys Lys Gln Val Leu
                165                 170                 175 aaa ggc ttg tgg tat ctt cat cat gag aag cat att att cac agg gat      576
Lys Gly Leu Trp Tyr Leu His His Glu Lys His Ile Ile His Arg Asp
            180                 185                 190 ttg aaa cct tcg aat ttg cta atc aat cac aga ggt gat gtc aaa atc      624
Leu Lys Pro Ser Asn Leu Leu Ile Asn His Arg Gly Asp Val Lys Ile
        195                 200                 205 aca gac ttt ggt gtg agt gca gta cta gca agc aca tct gga ctg gcc      672
Thr Asp Phe Gly Val Ser Ala Val Leu Ala Ser Thr Ser Gly Leu Ala
    210                 215                 220 aat acc ttt gtc ggc aca tac aac tat atg tct cca gag aga att tca      720
Asn Thr Phe Val Gly Thr Tyr Asn Tyr Met Ser Pro Glu Arg Ile Ser
225                 230                 235                 240 gga ggt gcc tat gat tac aaa agc gac att tgg agc ttg ggt tta gtc      768
Gly Gly Ala Tyr Asp Tyr Lys Ser Asp Ile Trp Ser Leu Gly Leu Val
                245                 250                 255 ttg ctc gag tgt gca aca ggt cat ttc cca tat aaa cca ccc gag gga      816
Leu Leu Glu Cys Ala Thr Gly His Phe Pro Tyr Lys Pro Pro Glu Gly
            260                 265                 270 gat gaa gga tgg gtc aat gtc tat gaa ctt atg gaa acc ata gtt gac      864
Asp Glu Gly Trp Val Asn Val Tyr Glu Leu Met Glu Thr Ile Val Asp
        275                 280                 285 caa cca gaa cct tgt gca cct cct gac caa ttt tct cca caa ttc tgc      912
Gln Pro Glu Pro Cys Ala Pro Pro Asp Gln Phe Ser Pro Gln Phe Cys
    290                 295                 300 tca ttc ata tct gca tgt gtc cag aag cac cag aag gac aga ctg tcg      960
Ser Phe Ile Ser Ala Cys Val Gln Lys His Gln Lys Asp Arg Leu Ser
305                 310                 315                 320 gca aat gat ctc atg agt cac cct ttc atc acc atg tac gat gac cag     1008
Ala Asn Asp Leu Met Ser His Pro Phe Ile Thr Met Tyr Asp Asp Gln
                325                 330                 335 gat atc gat ctt gga tct tac ttc act tcc gca gga cct cca ttg gca     1056
Asp Ile Asp Leu Gly Ser Tyr Phe Thr Ser Ala Gly Pro Pro Leu Ala
            340                 345                 350 aca ctt act gag cta taa                                              1074
Thr Leu Thr Glu Leu
        355

<210> SEQ ID NO 2
<211> LENGTH: 357
<212> TYPE: PRT
<213> ORGANISM: Lycopersicon esculentum

<400> SEQUENCE: 2

Met Lys Lys Gly Ser Phe Ala Pro Asn Leu Lys Leu Ser Leu Pro Pro
1               5                   10                  15

Pro Asp Glu Val Ala Leu Ser Lys Phe Leu Thr Glu Ser Gly Thr Phe
                20                  25                  30

Lys Asp Gly Asp Leu Leu Val Asn Arg Asp Gly Val Arg Ile Val Ser
            35                  40                  45

Gln Ser Glu Val Ala Ala Pro Ser Val Ile Gln Pro Ser Asp Asn Gln
        50                  55                  60

Leu Cys Leu Ala Asp Phe Glu Ala Val Lys Val Ile Gly Lys Gly Asn
```

```
                65                  70                  75                  80
Gly Gly Ile Val Arg Leu Val Gln His Lys Trp Thr Gly Gln Phe Phe
                        85                  90                  95
Ala Leu Lys Val Ile Gln Met Asn Ile Asp Glu Ser Met Arg Lys His
                100                 105                 110
Ile Ala Gln Glu Leu Arg Ile Asn Gln Ser Ser Gln Cys Pro Tyr Val
                115                 120                 125
Val Ile Cys Tyr Gln Ser Phe Phe Asp Asn Gly Ala Ile Ser Leu Ile
            130                 135                 140
Leu Glu Tyr Met Asp Gly Gly Ser Leu Ala Asp Phe Leu Lys Lys Val
145                 150                 155                 160
Lys Thr Ile Pro Glu Arg Phe Leu Ala Val Ile Cys Lys Gln Val Leu
                165                 170                 175
Lys Gly Leu Trp Tyr Leu His His Glu Lys His Ile Ile His Arg Asp
                180                 185                 190
Leu Lys Pro Ser Asn Leu Leu Ile Asn His Arg Gly Asp Val Lys Ile
                195                 200                 205
Thr Asp Phe Gly Val Ser Ala Val Leu Ala Ser Thr Gly Leu Ala
    210                 215                 220
Asn Thr Phe Val Gly Thr Tyr Asn Tyr Met Ser Pro Glu Arg Ile Ser
225                 230                 235                 240
Gly Gly Ala Tyr Asp Tyr Lys Ser Asp Ile Trp Ser Leu Gly Leu Val
                245                 250                 255
Leu Leu Glu Cys Ala Thr Gly His Phe Pro Tyr Lys Pro Pro Glu Gly
                260                 265                 270
Asp Glu Gly Trp Val Asn Val Tyr Glu Leu Met Glu Thr Ile Val Asp
                275                 280                 285
Gln Pro Glu Pro Cys Ala Pro Pro Asp Gln Phe Ser Pro Gln Phe Cys
    290                 295                 300
Ser Phe Ile Ser Ala Cys Val Gln Lys His Gln Lys Asp Arg Leu Ser
305                 310                 315                 320
Ala Asn Asp Leu Met Ser His Pro Phe Ile Thr Met Tyr Asp Asp Gln
                325                 330                 335
Asp Ile Asp Leu Gly Ser Tyr Phe Thr Ser Ala Gly Pro Pro Leu Ala
                340                 345                 350
Thr Leu Thr Glu Leu
            355

<210> SEQ ID NO 3
<211> LENGTH: 225
<212> TYPE: PRT
<213> ORGANISM: Arabidopsis thaliana

<400> SEQUENCE: 3

Leu Asp Met Val Lys Val Ile Gly Lys Gly Ser Ser Gly Val Val Gln
1               5                   10                  15
Leu Val Gln His Lys Trp Thr Gly Gln Phe Phe Ala Leu Lys Val Ile
                20                  25                  30
Gln Leu Asn Ile Asp Glu Ala Ile Arg Lys Ala Ile Ala Gln Glu Leu
            35                  40                  45
Lys Ile Asn Gln Ser Ser Gln Cys Pro Asn Leu Val Thr Ser Tyr Gln
        50                  55                  60
Ser Phe Tyr Asp Asn Gly Ala Ile Ser Leu Ile Leu Glu Tyr Met Asp
65                  70                  75                  80
```

```
Gly Gly Ser Leu Ala Asp Phe Leu Lys Ser Val Lys Arg His Ile Ile
             85                  90                  95

His Arg Asp Leu Lys Pro Ser Asn Leu Leu Ile Asn His Arg Gly Glu
            100                 105                 110

Val Lys Ile Thr Asp Phe Gly Val Ser Thr Val Met Thr Asn Thr Ala
            115                 120                 125

Gly Leu Ala Asn Thr Phe Val Gly Thr Tyr Asn Tyr Met Ser Pro Glu
130                 135                 140

Arg Ile Val Gly Asn Lys Tyr Gly Asn Lys Ser Asp Ile Trp Ser Leu
145                 150                 155                 160

Gly Leu Val Val Leu Glu Cys Ala Thr Gly Lys Phe Pro Tyr Ala Pro
            165                 170                 175

Pro Asn Gln Glu Glu Thr Trp Thr Ser Val Phe Glu Leu Met Glu Ala
            180                 185                 190

Ile Val Asp Gln Pro Pro Ala Leu Pro Ser Gly Asn Phe Ser Pro
            195                 200                 205

Glu Leu Ser Ser Phe Ile Ser Thr Cys Leu Gln Lys Glu Pro Asn Ser
    210                 215                 220

Arg
225

<210> SEQ ID NO 4
<211> LENGTH: 221
<212> TYPE: PRT
<213> ORGANISM: Nicotiana tabacum

<400> SEQUENCE: 4

Met Arg Val Phe Gly Ala Ile Gly Ser Gly Ala Ser Ser Val Val Gln
 1               5                  10                  15

Arg Ala Ile His Ile Pro Thr His Arg Ile Ile Ala Leu Lys Lys Ile
             20                  25                  30

Asn Ile Phe Glu Lys Glu Lys Arg Gln Gln Leu Leu Thr Glu Ile Arg
         35                  40                  45

Thr Leu Cys Glu Ala Pro Cys Cys Gln Gly Leu Val Glu Phe Tyr Gly
     50                  55                  60

Ala Phe Tyr Thr Pro Asp Ser Gly Gln Ile Ser Ile Ala Leu Glu Tyr
 65                  70                  75                  80

Met Asp Gly Gly Ser Leu Ala Asp Ile Ile Lys Val Arg Lys Arg His
                 85                  90                  95

Leu Val His Arg Asp Ile Lys Pro Ala Asn Leu Leu Val Asn Arg Lys
            100                 105                 110

Gly Glu Pro Lys Ile Thr Asp Phe Gly Ile Ser Ala Gly Leu Glu Ser
            115                 120                 125

Ser Ile Ala Met Cys Ala Thr Phe Val Gly Thr Val Thr Tyr Met Ser
130                 135                 140

Pro Glu Arg Ile Arg Asn Glu Asn Tyr Ser Tyr Pro Ala Asp Ile Trp
145                 150                 155                 160

Ser Leu Gly Leu Ala Leu Phe Glu Cys Gly Thr Gly Glu Phe Pro Tyr
            165                 170                 175

Thr Ala Asn Glu Gly Pro Val Asn Leu Met Leu Gln Ile Leu Asp Asp
            180                 185                 190

Pro Ser Pro Ser Leu Ser Gly His Glu Phe Ser Pro Glu Phe Cys Ser
            195                 200                 205

Phe Ile Asp Ala Cys Leu Lys Lys Asn Pro Asp Asp Arg
210                 215                 220
```

<210> SEQ ID NO 5
<211> LENGTH: 221
<212> TYPE: PRT
<213> ORGANISM: Arabidopsis thaliana

<400> SEQUENCE: 5

```
Met Arg Val Phe Gly Ala Ile Gly Ser Gly Ala Ser Ser Val Val Gln
 1               5                  10                  15

Arg Ala Ile His Ile Pro Asn His Arg Ile Leu Ala Leu Lys Lys Ile
             20                  25                  30

Asn Ile Phe Glu Arg Glu Lys Arg Gln Gln Leu Leu Thr Glu Ile Arg
         35                  40                  45

Thr Leu Cys Glu Ala Pro Cys His Glu Gly Leu Val Asp Phe His Gly
     50                  55                  60

Ala Phe Tyr Ser Pro Asp Ser Gly Gln Ile Ser Ile Ala Leu Glu Tyr
 65                  70                  75                  80

Met Asn Gly Gly Ser Leu Ala Asp Ile Leu Lys Val Thr Lys Arg His
                 85                  90                  95

Leu Val His Arg Asp Ile Lys Pro Ala Asn Leu Leu Ile Asn His Lys
            100                 105                 110

Gly Glu Pro Lys Ile Thr Asp Phe Gly Ile Ser Ala Gly Leu Glu Asn
        115                 120                 125

Ser Met Ala Met Cys Ala Thr Phe Val Gly Thr Val Thr Tyr Met Ser
130                 135                 140

Pro Glu Arg Ile Arg Asn Asp Ser Tyr Ser Tyr Pro Ala Asp Ile Trp
145                 150                 155                 160

Ser Leu Gly Leu Ala Leu Phe Glu Cys Gly Thr Gly Glu Phe Pro Tyr
                165                 170                 175

Ile Ala Asn Glu Gly Pro Val Asn Leu Met Leu Gln Ile Leu Asp Asp
            180                 185                 190

Pro Ser Pro Thr Pro Pro Lys Gln Glu Phe Ser Pro Glu Phe Cys Ser
        195                 200                 205

Phe Ile Asp Ala Cys Leu Gln Lys Asp Pro Asp Ala Arg
    210                 215                 220
```

<210> SEQ ID NO 6
<211> LENGTH: 286
<212> TYPE: PRT
<213> ORGANISM: Dictyostelium discoideum

<400> SEQUENCE: 6

```
Leu Lys Ile Ile Arg Val Leu Gly Arg Gly Ala Gly Gly Val Val Lys
 1               5                  10                  15

Leu Ala Tyr His Glu Thr Ser Gly Thr Tyr Ile Ala Leu Lys Val Ile
             20                  25                  30

Thr Leu Asp Ile Gln Glu Asn Ile Arg Lys Gln Ile Ile Leu Glu Leu
         35                  40                  45

Lys Thr Leu His Lys Thr Ser Tyr Pro Tyr Ile Val Ser Phe Tyr Asp
     50                  55                  60

Ala Phe Tyr Thr Glu Gly Ser Ile Phe Ile Ala Leu Glu Phe Met Glu
 65                  70                  75                  80

Leu Gly Ser Leu Ser Asp Ile Met Lys Lys Thr Ser Leu His Leu Ile
                 85                  90                  95

His Arg Asp Ile Lys Pro Ser Asn Ile Leu Val Asn Asn Lys Gly Glu
            100                 105                 110
```

```
Ala Lys Ile Ala Asp Phe Gly Val Ser Gly Gln Leu Gln His Thr Leu
        115                 120                 125

Ser Lys Ala Val Thr Trp Val Gly Thr Val Thr Tyr Met Ser Pro Glu
130                 135                 140

Arg Ile Ser Gly Arg Ser Tyr Ser Phe Asp Ser Asp Ile Trp Ser Leu
145                 150                 155                 160

Gly Leu Thr Ile Leu Glu Cys Ala Ile Gly Lys Phe Pro Tyr Gly Ser
                165                 170                 175

Asn Leu Pro His Gln Gln Gln Pro Leu Gln Gln Leu Gln Asn
                180                 185                 190

Leu Asp Ile Asn Asn Ser Asn Asn Ile Arg Asn Ser Asn Asn
                195                 200                 205

Asn Asn Asn Asn Asn Asn Asn Asn Asn Asn Asn Asn Asn
            210                 215                 220

Asn Asn Val Leu Asp Ile Ser Asn Gly Gly Leu Val Asp Ser Gly Ser
225                 230                 235                 240

Ser Val Pro Glu Gly Met Gly Phe Trp Val Leu Leu Asp Cys Ile Val
                245                 250                 255

Lys Glu Glu Val Pro Ile Leu Pro Ser Thr Phe Ser Lys Glu Phe Arg
                260                 265                 270

Ser Phe Ile Ser Glu Cys Leu Gln Lys Glu Pro Thr Glu Arg
                275                 280                 285

<210> SEQ ID NO 7
<211> LENGTH: 222
<212> TYPE: PRT
<213> ORGANISM: Leishmania donovani

<400> SEQUENCE: 7

Tyr Ser Ser Lys Arg Asn Val Gly Ala Gly Ala Ser Gly Asp Val Phe
  1               5                  10                  15

Phe Ala Arg Leu Lys Asn Gly Thr Ser Ile Ala Leu Lys Arg Ile Pro
                 20                  25                  30

Ile Ser Ser Lys Ala His Arg Asp Glu Val Asp Arg Glu Leu Gln Val
             35                  40                  45

Phe Met Ala Arg Ala Asp Ser Pro Tyr Val Met Asn Asn Tyr Gly Ala
         50                  55                  60

Phe Trp Asp Ala Glu Asp Asp Ala Ile Val Ile Pro Met Glu Trp Met
 65                  70                  75                  80

Pro Tyr Thr Val Lys Asp Leu Gly Leu Phe Trp Gly Lys Arg Val
                 85                  90                  95

Leu His Arg Asp Leu Lys Pro Ser Asn Leu Leu Ile Ser Glu Thr Gly
                100                 105                 110

His Val Lys Ile Ala Asp Phe Gly Val Ser Lys Leu Ile Gln Thr Leu
            115                 120                 125

Ala Val Ser Ser Thr Tyr Val Ala Thr Met Cys Phe Met Ala Pro Glu
        130                 135                 140

Arg Leu Glu Gln Gly Met Tyr Gly Phe Ser Ser Asp Val Trp Ser Leu
145                 150                 155                 160

Gly Leu Thr Met Ile Gly Ala Val Thr Gly Lys Asn Pro Trp Ala Pro
                165                 170                 175

Pro Glu Glu Met Asn Leu Tyr Gln Leu Leu Gly Lys Met Ala Asn Gly
                180                 185                 190

Ser Thr Pro Thr Leu Pro Lys Ser Gly Ala Phe Ser Asp Asp Val Lys
```

-continued

```
                195                 200                 205
Asp Phe Val Lys Gln Cys Leu Glu Arg Asp Pro Asp Thr Arg
    210                 215                 220

<210> SEQ ID NO 8
<211> LENGTH: 222
<212> TYPE: PRT
<213> ORGANISM: Drosophila melanogaster

<400> SEQUENCE: 8

Leu Lys His Leu Gly Asp Leu Gly Asn Gly Thr Ser Gly Asn Val Val
  1               5                  10                  15

Lys Met Met His Leu Ser Ser Asn Thr Ile Ile Ala Val Lys Gln Met
                 20                  25                  30

Arg Arg Thr Gly Asn Ala Glu Glu Asn Lys Arg Ile Leu Met Asp Leu
             35                  40                  45

Asp Val Val Leu Lys Ser His Asp Cys Lys Tyr Ile Val Lys Cys Leu
     50                  55                  60

Gly Cys Phe Val Arg Asp Pro Asp Val Trp Ile Cys Met Glu Leu Met
 65                  70                  75                  80

Ser Met Cys Phe Asp Lys Leu Leu Lys Leu Ser Lys His Gly Val Ile
                 85                  90                  95

His Arg Asp Val Lys Pro Ser Asn Ile Leu Ile Asp Glu Arg Gly Asn
            100                 105                 110

Ile Lys Leu Cys Asp Phe Gly Ile Ser Gly Arg Leu Val Asp Ser Lys
        115                 120                 125

Ala Asn Thr Arg Ala Gly Cys Ala Ala Tyr Met Ala Pro Glu Arg Ile
    130                 135                 140

Asp Pro Lys Lys Pro Lys Tyr Asp Ile Arg Ala Asp Val Trp Ser Leu
145                 150                 155                 160

Gly Ile Thr Leu Val Glu Leu Ala Thr Ala Arg Ser Pro Tyr Glu Gly
                165                 170                 175

Cys Asn Thr Asp Phe Glu Val Leu Thr Lys Val Leu Asp Ser Glu Pro
            180                 185                 190

Pro Cys Leu Pro Tyr Gly Glu Gly Tyr Asn Phe Ser Gln Gln Phe Arg
        195                 200                 205

Asp Phe Val Ile Lys Cys Leu Thr Lys Asn His Gln Asp Arg
    210                 215                 220

<210> SEQ ID NO 9
<211> LENGTH: 234
<212> TYPE: PRT
<213> ORGANISM: Homo sapiens

<400> SEQUENCE: 9

Phe Glu Lys Ile Ser Glu Leu Gly Ala Gly Asn Gly Gly Val Val Phe
  1               5                  10                  15

Lys Val Ser His Lys Pro Ser Gly Leu Val Met Ala Arg Lys Leu Ile
                 20                  25                  30

His Leu Glu Ile Lys Pro Ala Ile Arg Asn Gln Ile Ile Arg Glu Leu
             35                  40                  45

Gln Val Leu His Glu Cys Asn Ser Pro Tyr Ile Val Gly Phe Tyr Gly
     50                  55                  60

Ala Phe Tyr Ser Asp Gly Glu Ile Ser Ile Cys Met Glu His Met Asp
 65                  70                  75                  80

Gly Gly Ser Leu Asp Gln Val Leu Lys Lys Ala Gly His Lys Ile Met
```

```
                         85                    90                    95
His Arg Asp Val Lys Pro Ser Asn Ile Leu Val Asn Ser Arg Gly Glu
                100                 105                 110

Ile Lys Leu Cys Asp Phe Gly Val Ser Gly Gln Leu Ile Asp Ser Met
            115                 120                 125

Ala Asn Ser Phe Val Gly Thr Arg Ser Tyr Met Ser Pro Glu Arg Leu
130                 135                 140

Gln Gly Thr His Tyr Ser Val Gln Ser Asp Ile Trp Ser Met Gly Leu
145                 150                 155                 160

Ser Leu Val Glu Met Ala Val Gly Arg Tyr Pro Ile Pro Pro Pro Asp
                165                 170                 175

Ala Lys Glu Leu Glu Leu Met Phe Gly Gly Met Asp Ser Arg Pro Pro
                180                 185                 190

Met Ala Ile Phe Glu Leu Leu Asp Tyr Ile Val Asn Glu Pro Pro Pro
                195                 200                 205

Lys Leu Pro Ser Gly Val Phe Ser Leu Glu Phe Gln Asp Phe Val Asn
            210                 215                 220

Lys Cys Leu Ile Lys Asn Pro Ala Glu Arg
225                 230

<210> SEQ ID NO 10
<211> LENGTH: 177
<212> TYPE: PRT
<213> ORGANISM: Rattus norvegicus

<400> SEQUENCE: 10

Ile Arg Tyr Arg Asp Thr Leu Gly His Gly Asn Gly Gly Thr Val Tyr
1               5                   10                  15

Lys Ala Tyr His Val Pro Ser Gly Lys Ile Leu Ala Val Lys Val Ile
                20                  25                  30

Leu Leu Asp Ile Thr Leu Glu Leu Gln Lys Gln Ile Met Ser Glu Leu
            35                  40                  45

Glu Ile Leu Tyr Lys Cys Asp Ser Ser Tyr Ile Ile Gly Phe Tyr Gly
        50                  55                  60

Ala Phe Phe Val Glu Asn Arg Ile Ser Ile Cys Thr Glu Phe Met Asp
65                  70                  75                  80

Gly Gly Ser Leu Asp Val Tyr Arg Lys Ile Leu Lys Ile Leu His Arg
                85                  90                  95

Asp Val Lys Pro Ser Asn Met Leu Val Asn Thr Ser Gly Gln Val Lys
                100                 105                 110

Leu Cys Asp Phe Gly Val Ser Thr Gln Leu Val Asn Ser Ile Ala Lys
            115                 120                 125

Thr Tyr Val Gly Thr Asn Ala Tyr Met Ala Pro Glu Arg Ile Ser Gly
130                 135                 140

Glu Gln Tyr Gly Ile His Ser Asp Val Trp Ser Leu Gly Ile Ser Phe
145                 150                 155                 160

Met Glu Leu Ala Leu Gly Arg Phe Pro Tyr Pro Gln Ile Gln Lys Asn
                165                 170                 175

Gln

<210> SEQ ID NO 11
<211> LENGTH: 185
<212> TYPE: PRT
<213> ORGANISM: Homo sapiens

<400> SEQUENCE: 11
```

```
Leu Val Thr Ile Ser Glu Leu Gly Arg Gly Ala Tyr Gly Val Val Glu
  1               5                  10                  15

Lys Val Arg His Ala Gln Ser Gly Thr Ile Met Ala Val Lys Arg Ile
             20                  25                  30

Arg Ala Thr Val Asn Ser Gln Glu Gln Lys Arg Leu Leu Met Asp Leu
         35                  40                  45

Asp Ile Asn Met Arg Thr Val Asp Cys Phe Tyr Thr Val Thr Phe Tyr
     50                  55                  60

Gly Ala Leu Phe Arg Glu Gly Asp Val Trp Ile Cys Met Glu Leu Met
 65                  70                  75                  80

Asp Thr Ser Leu Asp Lys Phe Tyr Arg Lys Val Leu Asp Lys Asn Met
                 85                  90                  95

Leu Ser Val Ile His Arg Asp Val Lys Pro Ser Asn Val Leu Ile Asn
                100                 105                 110

Lys Glu Gly His Val Lys Met Cys Asp Phe Gly Ile Ser Gly Tyr Leu
            115                 120                 125

Val Asp Ser Val Ala Lys Thr Met Asp Ala Gly Cys Lys Pro Tyr Met
        130                 135                 140

Ala Pro Glu Arg Ile Asn Pro Glu Leu Asn Gln Lys Gly Tyr Asn Val
145                 150                 155                 160

Lys Ser Asp Val Trp Ser Leu Gly Ile Thr Met Ile Glu Met Ala Ile
                165                 170                 175

Leu Arg Phe Pro Tyr Glu Ser Trp Gly
                180                 185

<210> SEQ ID NO 12
<211> LENGTH: 184
<212> TYPE: PRT
<213> ORGANISM: Saccharomyces cerevisiae

<400> SEQUENCE: 12

Leu Glu Phe Leu Asp Glu Leu Gly His Gly Asn Tyr Gly Asn Val Ser
  1               5                  10                  15

Lys Val Leu His Lys Pro Thr Asn Val Ile Met Ala Thr Lys Glu Val
             20                  25                  30

Arg Leu Glu Leu Asp Glu Ala Lys Phe Arg Gln Ile Leu Met Glu Leu
         35                  40                  45

Glu Val Leu His Lys Cys Asn Ser Pro Tyr Ile Val Asp Phe Tyr Gly
     50                  55                  60

Ala Phe Phe Ile Glu Gly Ala Val Tyr Met Cys Met Glu Tyr Met Asp
 65                  70                  75                  80

Gly Gly Ser Leu Asp Lys Ile Tyr Asp Glu Ser Ser Glu Ile Gly His
                 85                  90                  95

Asn Ile Ile His Arg Asp Val Lys Pro Thr Asn Ile Leu Cys Ser Ala
                100                 105                 110

Asn Gln Gly Thr Val Lys Leu Cys Asp Phe Gly Val Ser Gly Asn Leu
            115                 120                 125

Val Ala Ser Leu Ala Lys Thr Asn Ile Gly Cys Gln Ser Tyr Met Ala
        130                 135                 140

Pro Glu Arg Ile Lys Ser Leu Asn Pro Asp Arg Ala Thr Tyr Thr Val
145                 150                 155                 160

Gln Ser Asp Ile Trp Ser Leu Gly Leu Ser Ile Leu Glu Met Ala Leu
                165                 170                 175

Gly Arg Tyr Pro Tyr Pro Pro Glu
```

180

<210> SEQ ID NO 13
<211> LENGTH: 189
<212> TYPE: PRT
<213> ORGANISM: Saccharomyces cerevisiae

<400> SEQUENCE: 13

Leu Val Gln Leu Gly Lys Ile Gly Ala Gly Asn Ser Gly Thr Val Val
1               5                   10                  15

Lys Ala Leu His Val Pro Asp Ser Lys Ile Val Ala Lys Lys Thr Ile
            20                  25                  30

Pro Val Glu Gln Asn Asn Ser Thr Ile Ile Asn Gln Leu Val Arg Glu
        35                  40                  45

Leu Ser Ile Val Lys Asn Val Lys Pro His Glu Asn Ile Ile Thr Phe
    50                  55                  60

Tyr Gly Ala Tyr Tyr Asn Gln His Ile Asn Asn Glu Ile Ile Ile Leu
65                  70                  75                  80

Met Glu Tyr Ser Asp Cys Gly Ser Leu Asp Lys Ile Leu Ser Val Tyr
                85                  90                  95

Lys Arg Phe Val Gln Arg Gly Thr Val Tyr Lys Ile Ile His Arg Asp
            100                 105                 110

Ile Lys Pro Ser Asn Val Leu Ile Asn Ser Lys Gly Gln Ile Lys Leu
        115                 120                 125

Cys Asp Phe Gly Val Ser Lys Lys Leu Ile Asn Ser Ile Ala Asp Thr
    130                 135                 140

Phe Val Gly Thr Ser Thr Tyr Met Ser Pro Glu Arg Ile Gln Gly Asn
145                 150                 155                 160

Val Tyr Ser Ile Lys Gly Asp Val Trp Ser Leu Gly Leu Met Ile Ile
                165                 170                 175

Glu Leu Val Thr Gly Glu Phe Pro Leu Gly Gly His Asn
            180                 185

<210> SEQ ID NO 14
<211> LENGTH: 189
<212> TYPE: PRT
<213> ORGANISM: Candida albicans

<400> SEQUENCE: 14

Leu Leu Thr Leu Lys Gln Leu Gly Ser Gly Asn Ser Gly Ser Val Ser
1               5                   10                  15

Lys Ile Leu His Ile Pro Thr Gln Lys Thr Met Ala Lys Lys Ile Ile
            20                  25                  30

His Ile Asp Ser Lys Ser Val Ile Gln Thr Gln Ile Ile Arg Glu Leu
        35                  40                  45

Arg Ile Leu His Glu Cys His Ser Pro Tyr Ile Ile Glu Phe Tyr Gly
    50                  55                  60

Ala Cys Leu Asn Asn Asn Asn Thr Ile Val Ile Cys Met Glu Tyr Cys
65                  70                  75                  80

Asn Cys Gly Ser Leu Asp Lys Ile Leu Pro Leu Cys Glu Asn His Lys
                85                  90                  95

Ile Ile His Arg Asp Ile Lys Pro Asn Asn Val Leu Met Thr His Lys
            100                 105                 110

Gly Glu Phe Lys Leu Cys Asp Phe Gly Val Ser Arg Glu Leu Thr Asn
        115                 120                 125

Ser Leu Ala Met Ala Asp Thr Phe Val Gly Thr Ser Met Tyr Met Ser

```
              130                 135                 140
Pro Glu Arg Ile Gln Gly Leu Asp Tyr Gly Val Lys Ser Asp Val Trp
145                 150                 155                 160

Ser Thr Gly Leu Met Leu Ile Glu Leu Ala Ser Gly Val Pro Val Trp
                165                 170                 175

Ser Glu Asp Asp Asn Asn Asn Asp Asp Glu Asp Asp
                180                 185

<210> SEQ ID NO 15
<211> LENGTH: 187
<212> TYPE: PRT
<213> ORGANISM: Saccharomyces cerevisiae

<400> SEQUENCE: 15

Ile Glu Thr Leu Gly Ile Leu Gly Glu Gly Ala Gly Gly Ser Val Ser
1               5                   10                  15

Lys Cys Lys Leu Lys Asn Gly Ser Lys Ile Phe Ala Leu Lys Val Ile
                20                  25                  30

Asn Thr Leu Asn Thr Asp Pro Glu Tyr Gln Lys Gln Ile Phe Arg Glu
            35                  40                  45

Leu Gln Phe Asn Arg Ser Phe Gln Ser Glu Tyr Ile Val Arg Tyr Tyr
        50                  55                  60

Gly Met Phe Thr Asp Asp Glu Asn Ser Ser Ile Tyr Ile Ala Met Glu
65                  70                  75                  80

Tyr Met Gly Gly Arg Ser Leu Asp Ala Ile Tyr Lys Asn Leu Leu Glu
                85                  90                  95

Arg Gly Gly Lys Lys Val Ile His Arg Asp Ile Lys Pro Gln Asn Ile
            100                 105                 110

Leu Leu Asn Glu Asn Gly Gln Val Lys Leu Cys Asp Phe Gly Val Ser
        115                 120                 125

Gly Glu Ala Val Asn Ser Leu Ala Thr Thr Phe Thr Gly Thr Ser Phe
130                 135                 140

Tyr Met Ala Pro Glu Arg Ile Gln Gly Gln Pro Tyr Ser Val Thr Ser
145                 150                 155                 160

Asp Val Trp Ser Leu Gly Leu Thr Ile Leu Glu Val Ala Asn Gly Lys
                165                 170                 175

Phe Pro Cys Ser Ser Glu Lys Met Ala Ala Asn
            180                 185

<210> SEQ ID NO 16
<211> LENGTH: 133
<212> TYPE: PRT
<213> ORGANISM: Arabidopsis thaliana

<400> SEQUENCE: 16

Arg His Ile Val His Arg Asp Ile Lys Pro Ser Asp Leu Leu Ile Asn
1               5                   10                  15

Ser Ala Lys Asn Val Lys Ile Ala Asp Phe Gly Val Ser Arg Ile Leu
                20                  25                  30

Ala Gln Thr Met Asp Pro Cys Asn Ser Ser Val Gly Thr Ile Ala Tyr
            35                  40                  45

Met Ser Pro Glu Arg Ile Asn Thr Asp Leu Asn His Gly Arg Tyr Asp
        50                  55                  60

Gly Tyr Ala Gly Asp Val Trp Ser Leu Gly Val Ser Ile Leu Glu Phe
65                  70                  75                  80

Tyr Leu Gly Arg Phe Pro Phe Ala Val Ser Arg Gln Gly Asp Trp Ala
```

85                  90                  95
Ser Leu Met Cys Ala Ile Cys Met Ser Gln Pro Pro Glu Ala Pro Ala
                100                 105                 110

Thr Ala Ser Gln Glu Phe Arg His Phe Val Ser Cys Cys Leu Gln Ser
            115                 120                 125

Asp Pro Pro Lys Arg
        130

<210> SEQ ID NO 17
<211> LENGTH: 133
<212> TYPE: PRT
<213> ORGANISM: Arabidopsis thaliana

<400> SEQUENCE: 17

Arg His Ile Val His Arg Asp Ile Lys Pro Ser Asn Leu Leu Ile Asn
  1               5                  10                  15

Ser Ala Lys Asn Val Lys Ile Ala Asp Phe Gly Val Ser Arg Ile Leu
                20                  25                  30

Ala Gln Thr Met Asp Pro Cys Asn Ser Ser Val Gly Thr Ile Ala Tyr
            35                  40                  45

Met Ser Pro Glu Arg Ile Asn Thr Asp Leu Asn Gln Gly Lys Tyr Asp
        50                  55                  60

Gly Tyr Ala Gly Asp Ile Trp Ser Leu Gly Val Ser Ile Leu Glu Phe
 65                  70                  75                  80

Tyr Leu Gly Arg Phe Pro Phe Pro Val Ser Arg Gln Gly Asp Trp Ala
                 85                  90                  95

Ser Leu Met Cys Ala Ile Cys Met Ser Gln Pro Pro Glu Ala Pro Ala
                100                 105                 110

Thr Ala Ser Pro Glu Phe Arg His Phe Ile Ser Cys Cys Leu Gln Arg
            115                 120                 125

Glu Pro Gly Lys Arg
        130

<210> SEQ ID NO 18
<211> LENGTH: 133
<212> TYPE: PRT
<213> ORGANISM: Lycopersicon esculentum

<400> SEQUENCE: 18

Arg Arg Ile Ile His Arg Asp Leu Lys Pro Ser Asn Leu Leu Ile Asn
  1               5                  10                  15

His Arg Gly Glu Val Lys Ile Thr Asp Phe Gly Val Ser Lys Ile Leu
                20                  25                  30

Thr Ser Thr Ser Ser Leu Ala Asn Ser Phe Val Gly Thr Tyr Pro Tyr
            35                  40                  45

Met Ser Pro Glu Arg Ile Ser Gly Ser Leu Tyr Ser Asn Lys Ser Asp
        50                  55                  60

Ile Trp Ser Leu Gly Leu Val Leu Leu Glu Cys Ala Thr Gly Lys Phe
 65                  70                  75                  80

Pro Tyr Thr Pro Pro Glu His Lys Lys Gly Trp Ser Ser Val Tyr Glu
                 85                  90                  95

Leu Val Asp Ala Ile Val Glu Asn Pro Pro Cys Ala Pro Ser Asn
                100                 105                 110

Leu Phe Ser Pro Glu Phe Cys Ser Phe Ile Ser Gln Cys Val Gln Lys
            115                 120                 125

Asp Pro Arg Asp Arg

```
   130

<210> SEQ ID NO 19
<211> LENGTH: 133
<212> TYPE: PRT
<213> ORGANISM: Lycopersicon esculentum

<400> SEQUENCE: 19

Lys His Ile Ile His Arg Asp Leu Lys Pro Ser Asn Leu Leu Ile Asn
  1               5                  10                  15

His Arg Gly Asp Val Lys Ile Thr Asp Phe Gly Val Ser Ala Val Leu
             20                  25                  30

Ala Ser Thr Ser Gly Leu Ala Asn Thr Phe Val Gly Thr Tyr Asn Tyr
         35                  40                  45

Met Ser Pro Glu Arg Ile Ser Gly Gly Ala Tyr Asp Tyr Lys Ser Asp
 50                  55                  60

Ile Trp Ser Leu Gly Leu Val Leu Leu Glu Cys Ala Thr Gly His Phe
 65                  70                  75                  80

Pro Tyr Lys Pro Pro Glu Gly Asp Glu Gly Trp Val Asn Val Tyr Glu
                 85                  90                  95

Leu Met Glu Thr Ile Val Asp Gln Pro Glu Pro Cys Ala Pro Pro Asp
            100                 105                 110

Gln Phe Ser Pro Gln Phe Cys Ser Phe Ile Ser Ala Cys Val Gln Lys
        115                 120                 125

His Gln Lys Asp Arg
    130

<210> SEQ ID NO 20
<211> LENGTH: 132
<212> TYPE: PRT
<213> ORGANISM: Zea mays

<400> SEQUENCE: 20

Arg His Val Ile His Arg Asp Ile Lys Pro Ser Asn Leu Leu Val Asn
  1               5                  10                  15

Lys Lys Gly Glu Val Lys Ile Thr Asp Phe Gly Val Ser Ala Val Leu
             20                  25                  30

Ala Ser Ser Ile Gly Gln Arg Asp Thr Phe Val Gly Thr Tyr Asn Tyr
         35                  40                  45

Met Ala Pro Glu Arg Ile Ser Gly Ser Thr Tyr Asp Tyr Lys Ser Asp
 50                  55                  60

Ile Trp Ser Leu Gly Leu Val Ile Leu Glu Cys Ala Ile Gly Arg Phe
 65                  70                  75                  80

Pro Tyr Ile Pro Ser Glu Gly Glu Gly Trp Leu Ser Phe Tyr Glu Leu
                 85                  90                  95

Leu Glu Ala Ile Val Asp Gln Pro Pro Pro Ser Ala Pro Ala Asp Gln
            100                 105                 110

Phe Ser Pro Glu Phe Cys Ser Phe Ile Ser Ser Cys Ile Gln Lys Asp
        115                 120                 125

Pro Ala Gln Arg
    130

<210> SEQ ID NO 21
<211> LENGTH: 88
<212> TYPE: PRT
<213> ORGANISM: Unknown
<220> FEATURE:
<223> OTHER INFORMATION: Description of Unknown Organism: another MAPKK
```

-continued

```
                        gene

<400> SEQUENCE: 21

Asp Thr Phe Thr Gly Thr Tyr Asn Tyr Met Ala Pro Glu Arg Ile Ser
 1               5                  10                  15

Gly Gln Lys His Gly Tyr Met Ser Asp Ile Trp Ser Leu Gly Leu Val
            20                  25                  30

Met Leu Glu Leu Ala Thr Gly Glu Phe Pro Tyr Pro Pro Arg Glu Ser
        35                  40                  45

Phe Tyr Glu Leu Leu Glu Ala Val Val Asp His Pro Pro Pro Ser Ala
    50                  55                  60

Pro Ser Asp Gln Phe Ser Glu Glu Phe Cys Ser Phe Val Ser Ala Cys
65                  70                  75                  80

Ile Gln Lys Asn Ala Ser Asp Arg
                85

<210> SEQ ID NO 22
<211> LENGTH: 59
<212> TYPE: DNA
<213> ORGANISM: Artificial Sequence
<220> FEATURE:
<223> OTHER INFORMATION: Description of Artificial Sequence:primer

<400> SEQUENCE: 22
gtatgtgccg acaaagtcat tggccagtcc atctgtgctt gctagtactg cactcacac          59

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence:primer

<400> SEQUENCE: 23
gtactagcaa gcacagatgg actggccaat gactttgtcg gcacatacaa ctatatgtc          59

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:nucleic acid
      sequence

<400> SEQUENCE: 24
ctctagagga tccccgggtg gtcagtccct t                                         31
```